(12) United States Patent
Cohen et al.

(10) Patent No.: US 6,257,091 B1
(45) Date of Patent: Jul. 10, 2001

(54) AUTOMATIC DECAPPER

(75) Inventors: Beri Cohen, Hartsdale; Thomas W. DeYoung, Stormville; Paul E. Purpura, Yorktown, all of NY (US); Helmut Artus, Gera (DE)

(73) Assignee: Bayer Corporation, Tarrytown, NY (US)

( * ) Notice: Subject to any disclaimer, the term of this patent is extended or adjusted under 35 U.S.C. 154(b) by 0 days.

(21) Appl. No.: 09/115,777

(22) Filed: Jul. 14, 1998

(51) Int. Cl.[7] ............................................. B67B 7/00
(52) U.S. Cl. ................... 81/3.2; 81/3.37; 81/3.39; 81/3.44
(58) Field of Search .................. 81/3.2, 3.36, 3.37, 81/3.39, 3.44, 90.1, 91.1, 128

(56) References Cited

U.S. PATENT DOCUMENTS

| | | | |
|---|---|---|---|
| 1,424,607 | * 8/1922 | Wisenberg | 81/3.39 |
| 2,524,434 | * 10/1950 | Duket | 81/3.44 X |
| 3,229,553 | * 1/1966 | Frederickson | 81/3.44 |

(List continued on next page.)

FOREIGN PATENT DOCUMENTS

| | | |
|---|---|---|
| 2212659 | 9/1973 | (DE) . |
| 2610209 | 9/1977 | (DE) . |
| 0736481 | 10/1996 | (EP) . |
| 1518492 | 7/1978 | (GB) . |
| 05221487 | 8/1993 | (JP) . |

OTHER PUBLICATIONS 1.11 Zubehör für Vacutainer—Röhrchen, Catalog Number 704999—Becton Dickinson (1 p.).

ACR–60—The Automatic Cap Remover—Terumo (Deutschland) GmbH (2 pp.).
COSENSE—ML—102 Ultrasonic Micro Measurement System—Cosense Inc. Hauppauge, NY (12 pp.).

*Primary Examiner*—James G. Smith
(74) *Attorney, Agent, or Firm*—Andrew L. Klawitter, Esq.; Rodman & Rodman

(57) ABSTRACT

An automatic decapper removes caps from capped test tubes by gripping the cap on a test tube with the upper grippers and holding the cap stationary while the test tube is rotated and translated downward with lower grippers. In a preferred embodiment, the upper grippers comprise three jaws coupled to a cam to be moved, as appropriate, from a first position in which a test tube cap may be inserted between the jaws to a second position in which the jaws grip the inserted cap. The upper grippers are mounted to a decapping arm that is pivotable between a first position above the lower grippers, in which the decapping takes place, to a second position above the exterior of the decapper, where it remains while the test tube is inserted into or removed from the lower grippers and where a removed cap may be released into a container for disposal or reuse. The lower grippers comprise a pair of lever arms for holding the test tube. The lower grippers form part of a rotatable assembly that moves up towards the upper grippers and down away from the upper grippers along a lead screw. A pair of half-gears mounted at a fixed vertical position are used to separate the lever arms for insertion and removal of the test tube when the rotatable assembly is vertically positioned with the lever arms adjacent the half-gears. An ultrasonic sensor may be positioned on the decapping arm above the upper grippers to detect the liquid level of the sample in the test tube after the cap has been removed and the decapping arm is returned to its first position. A liquid sensor comprising a prism and two fiber optic cables is mounted in a reservoir under lower grippers and is used to detect if there has been spillage from a test tube in the lower grippers.

24 Claims, 29 Drawing Sheets

U.S. PATENT DOCUMENTS

| | | |
|---|---|---|
| 3,587,208 | 6/1971 | Berry et al. . |
| 3,589,103 | 6/1971 | Calvillo et al. . |
| 3,664,213 * | 5/1972 | Anati ................................. 81/128 X |
| 3,803,795 | 4/1974 | Ouellette . |
| 3,844,093 | 10/1974 | Cato . |
| 3,852,867 | 12/1974 | Risener . |
| 3,914,920 | 10/1975 | DiIanni . |
| 3,987,535 | 10/1976 | Brown . |
| 4,030,271 | 6/1977 | Kefauver et al. . |
| 4,171,650 | 10/1979 | Cardinal . |
| 4,172,397 | 10/1979 | Herbert . |
| 4,178,732 | 12/1979 | Pfleger . |
| 4,217,798 | 8/1980 | McCarthy et al. . |
| 4,522,089 | 6/1985 | Alvi . |
| 4,620,411 | 11/1986 | Schieser et al. . |
| 4,676,712 | 6/1987 | Hayward et al. . |
| 4,773,285 | 9/1988 | Dionne . |
| 4,935,621 | 6/1990 | Pikulski . |
| 4,982,553 | 1/1991 | Itoh . |
| 5,080,864 | 1/1992 | Shaw . |
| 5,340,544 * | 8/1994 | Nishikawa .......................... 81/3.2 X |
| 5,345,844 | 9/1994 | Marsaw . |
| 5,366,896 | 11/1994 | Margrey et al. . |
| 5,370,019 | 12/1994 | Sartell et al. . |
| 5,380,486 | 1/1995 | Anami . |
| 5,481,946 * | 1/1996 | Nishikawa et al. ..................... 81/3.2 |
| 5,507,178 | 4/1996 | Dam . |
| 5,623,415 | 4/1997 | O'Bryan et al. . |
| 5,628,962 | 5/1997 | Kanbara et al. . |
| 5,735,181 | 4/1998 | Anderson . |
| 5,784,933 * | 7/1998 | Persellin ................................. 81/3.36 |

* cited by examiner

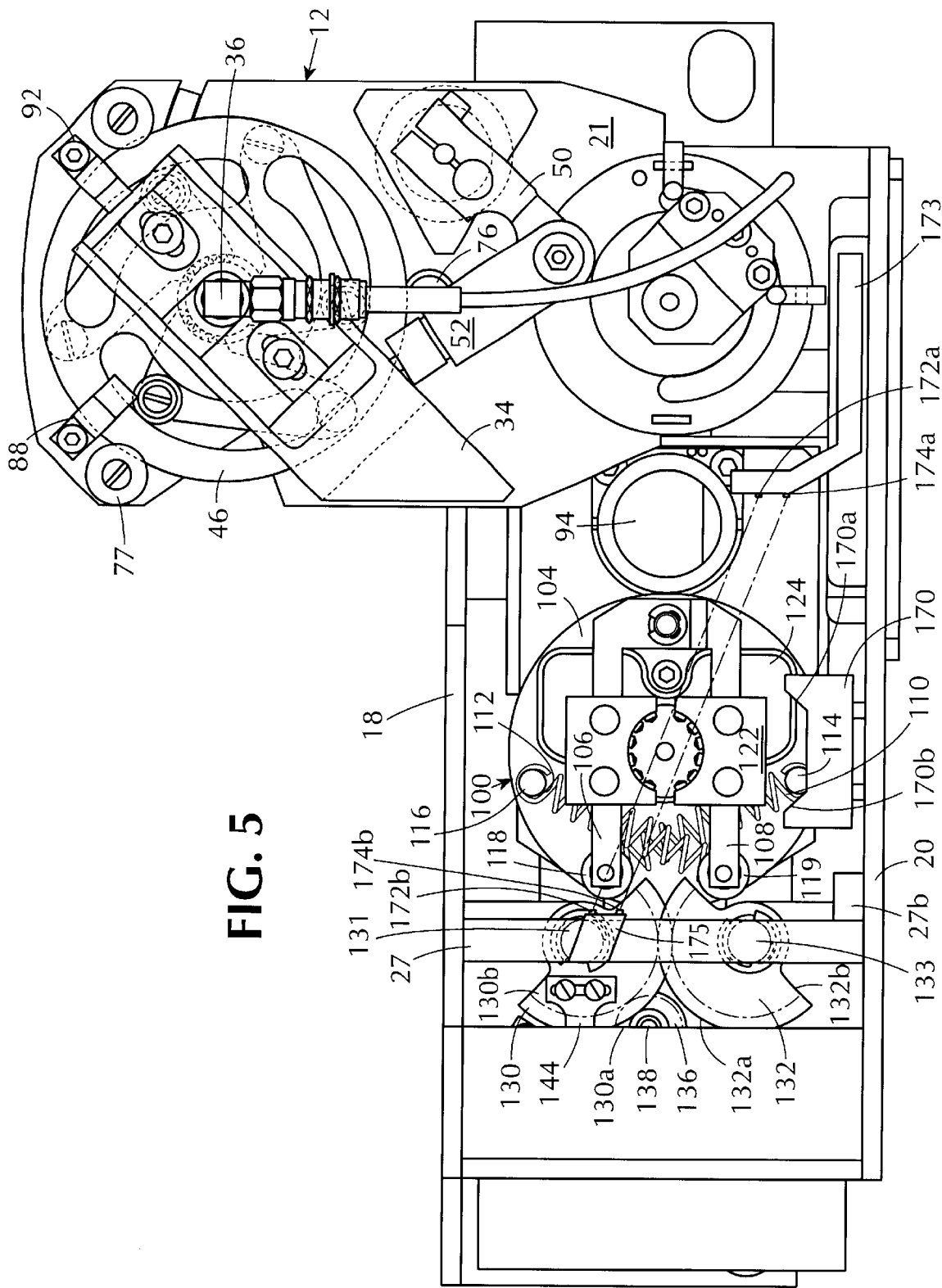

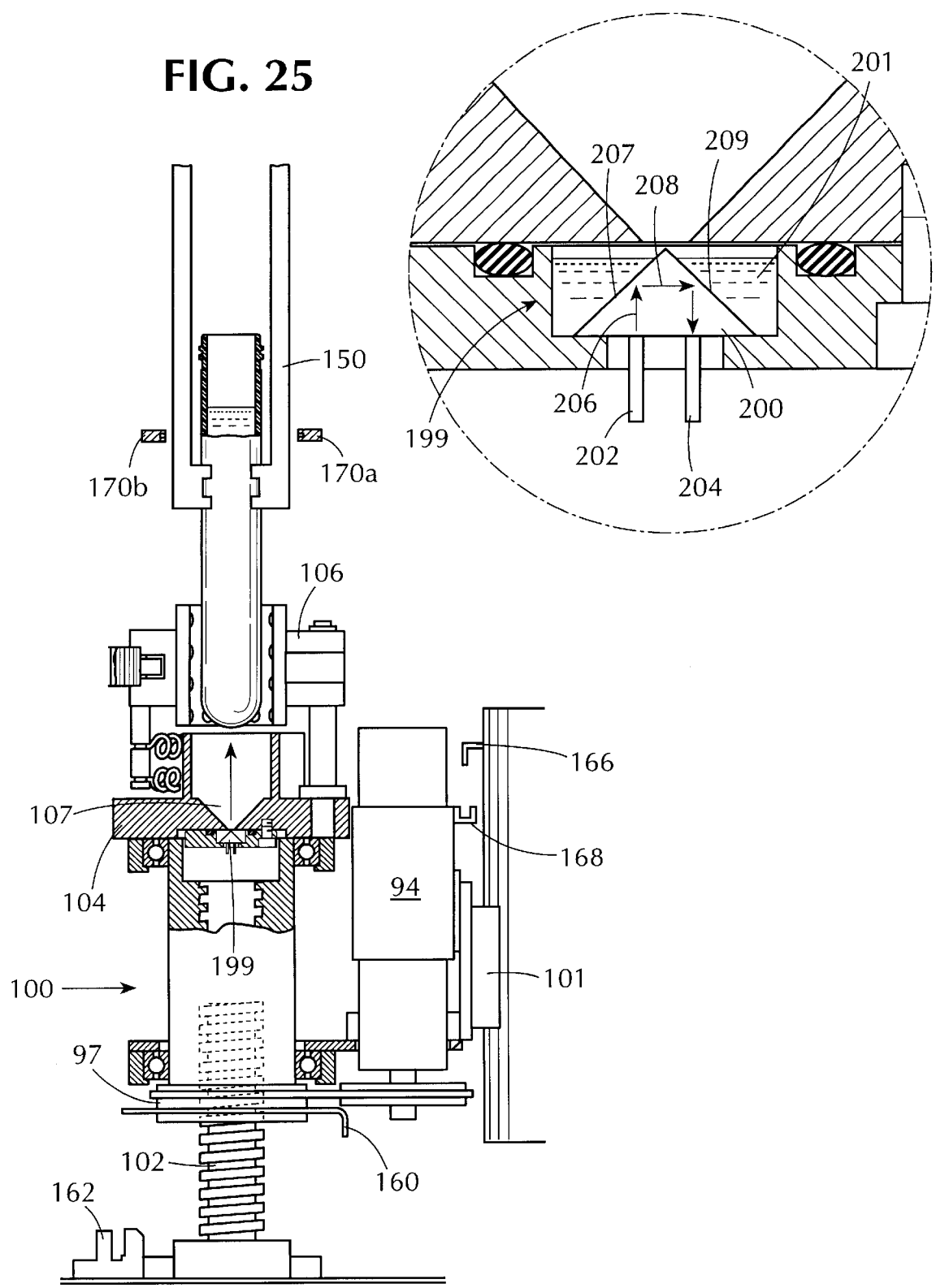

AUTOMATIC DECAPPER

FIELD OF THE INVENTION

This invention relates to an automatic decapper for decapping a variety of caps, including pull-off or screw-on caps, from test tubes of various types and sizes.

CROSS-REFERENCE TO RELATED APPLICATIONS

This application is related to the following U.S. patent applications, having the indicated titles, commonly assigned to the Bayer Corporation of Tarrytown, N.Y. and incorporated by reference herein:

Utility patent applications for Automatic Handler for Feeding Containers Into and Out of An Analytical Instrument ("Sample Handler"), Ser. No. 09/115,391, filed Jul. 14, 1998, Dynamic Noninvasive Detection of Analytical Container Features Using Ultrasound, Ser. No. 09/115,393, filed Jul. 14, 1998; Robotics for Transporting Containers and Objects Within An Automated Analytical Instrument and Service Tool for Servicing Robotics ("Robotics"), Ser. No. 09/115,080 filed Jul. 14, 1998; and Stat Shuttle Adapter and Transport Device, Ser. No. 09/113,640, filed Jul. 10, 1998.

BACKGROUND OF THE INVENTION

Analytical instruments should be as versatile as possible to minimize the number of different analytical instruments required in a single location, such as at a hospital or laboratory. It is therefore desirable to have an analytical instrument that handles test tubes of various types and sizes and both open ("uncapped") and closed ("capped") test tubes. Where the instrument requires the test tubes to be open before they are pretreated, sampled and tested, the instrument should have an automatic decapper to automatically decap closed test tubes. (As used herein, open test tubes, which do not require decapping, include containers like Microtainer holders® and Ezee Nest® inserts.)

Automating the decapping of test tubes is complicated by the variety of available test tubes, which may vary in diameter, height, and especially the variety of available caps to cover the test tubes. Some caps unscrew from threading on the top of the test tubes. These include caps for test tube-specific caps manufactured by Sarstedt of Germany, Braun, also of Germany, Meditech, Inc. of Bel Air, Md., and Greiner, as well as HemaGuard® caps used on Vacutainer® test tubes from Becton Dickinson. Another type of cap is a rubber stopper inserted into a test tube, such as a Vacutainer® test tube, which is removed by a pulling motion. The caps may also differ in their composition—they may be rubber, plastic, etc. A single decapper that can decap all of these tubes is needed because it is impractical to provide separate decappers in a single instrument for each type of cap.

In decapping the tubes, care must be taken not to break the tubes, generally made from glass or plastic, and not to spill any of the sample. There is a further constraint that portions of the sample and vapors not be transmitted to other tubes in the instrument which would interfere with the testing and analysis of the samples.

Automatic decappers have not previously been designed to remove from test tubes both screw-on caps and caps that must be pulled out. Generally, decappers have only been designed to decap test tubes sold by the same manufacturer. In one such system, Becton-Dickinson Model 704999 illustrated in a recent catalog in Germany, it appears that only Vacutainer® test tubes with rubber stoppers may be decapped. In another automatic decapper manufactured by Sarstedt, only screw-on caps on Sarstedt test tubes may be automatically removed with Sarstedt's decapper. Yet another automatic decapper from Terumo of Japan only decaps VenoJect test tubes manufactured by Terumo, which have a foil cap that must be cut off with a knife edge.

SmithKline Beecham Corporation also manufactures an automatic decapper for decapping test tubes but this decapper, which is designed for use as a station along a laboratory automation transport line, only pulls rubber stopper caps upwards and off of test tubes that are held in a stationary position. This decapper is not well-suited to be incorporated into a reasonably-sized analytical instrument as it is relatively large.

It would therefore be advantageous to have a decapper incorporated into an analytical instrument to decap test tubes both when an instrument is operated independently or as a backup decapper where the instrument interfaces with a lab automation system, should a freestanding decapper stationed along the transport line malfunction. While the space occupied by current freestanding decappers for use with a lab automation transport line may be relatively large, the decapper incorporated into an analytical instrument must be relatively compact to keep the instrument to a reasonable size. It should also be removable from the instrument for easy cleaning.

SUMMARY OF THE INVENTION

It is an object of this invention to provide an automatic decapper that may decap a wide variety of caps on a test tube that is removable by unscrewing or pulling off the cap.

The present invention is directed to an automatic decapper for removing a cap from a test tube. In a first aspect of the invention, the decapper has upper grippers having a first position to grip the cap and maintain the cap in a stationary position, lower grippers having a first position to grip the test tube and spaced from the upper grippers, and means for rotating the lower grippers relative to and translated away from the upper grippers while the upper grippers hold the cap stationary and the lower grippers grip the test tube to remove the cap from the test tube. The rotating means preferably comprises a rotatable assembly that may be rotated and translated with respect to a lead screw to which the rotatable assembly is coupled. The upper grippers may be mounted to a decapping arm that is pivotable between a first position above the lower grippers in which the test tube may be decapped and a second position that allows a test tube to be inserted into the lower grippers and to release a removed cap for disposal.

In another aspect of the invention, the decapper has upper grippers, lower grippers and means for moving the lower grippers relative to the upper grippers to remove the cap from the test tube. The upper grippers comprise a rotatable disk, which has a plurality of arcuate slots, a plurality of retractable jaws coupled to the slots in the disk, and a means for rotating the disk to move the jaws. The rotating means causes the jaws to pivot to a gripping position to grip the cap during the decapping of the test tube and to pivot to a retracted position at other times. In this aspect of the invention, the decapper may likewise comprise a decapping arm. Apertures in the decapping arm permit an ultrasonic sensor positioned above the apertures to determine a height level of a sample in the tube after the test tube has been decapped.

In another aspect of the invention, the decapper has upper grippers, lower grippers having a pair of lever arms biased together toward a closed position to grip a test tube, a pair of half-gears that are rotatable to push apart the pair of lever arms from the closed position to the open position to accept or release a test tube when the pair of lever arms are adjacent the half-gears, and means for moving the lower grippers relative to the upper grippers to remove the cap from the test tube.

The present invention is also directed to a sensor to detect the presence of liquid in a reservoir that may be located under a test tube placed within the lower grippers. The sensor comprises a prism having three sides, the first side being mounted flush with the bottom of the reservoir. A first fiber optic cable is positioned normal to the first side of the prism and transmits light into the first side of the prism and toward the second side of the prism. If there is liquid in the reservoir, at least a portion of the light emitted by the first fiber optic cable will be reflected from the second side toward the third side of the prism and then reflected from the third side of the prism back toward a second location under the first side of the prism, where a second fiber optic cable is positioned.

BRIEF DESCRIPTION OF THE DRAWINGS

The inventions and modifications thereof will become better evident from the detailed description below in conjunction with the following figures, in which like reference characters refer to like elements, and in which:

FIG. 5 is a top view of the decapper with the decapping arm in the first position with no test tube between rotatable lower grippers;

FIG. 24 is a cross-sectional view of a sensor at bottom of the lower grippers to detect spills from test tubes;

FIG. 25 is a rear view of the lower grippers with the fingers on the robotic arm removing the test tube from the decapper;

DESCRIPTION OF THE PREFERRED EMBODIMENT

Figure 1:
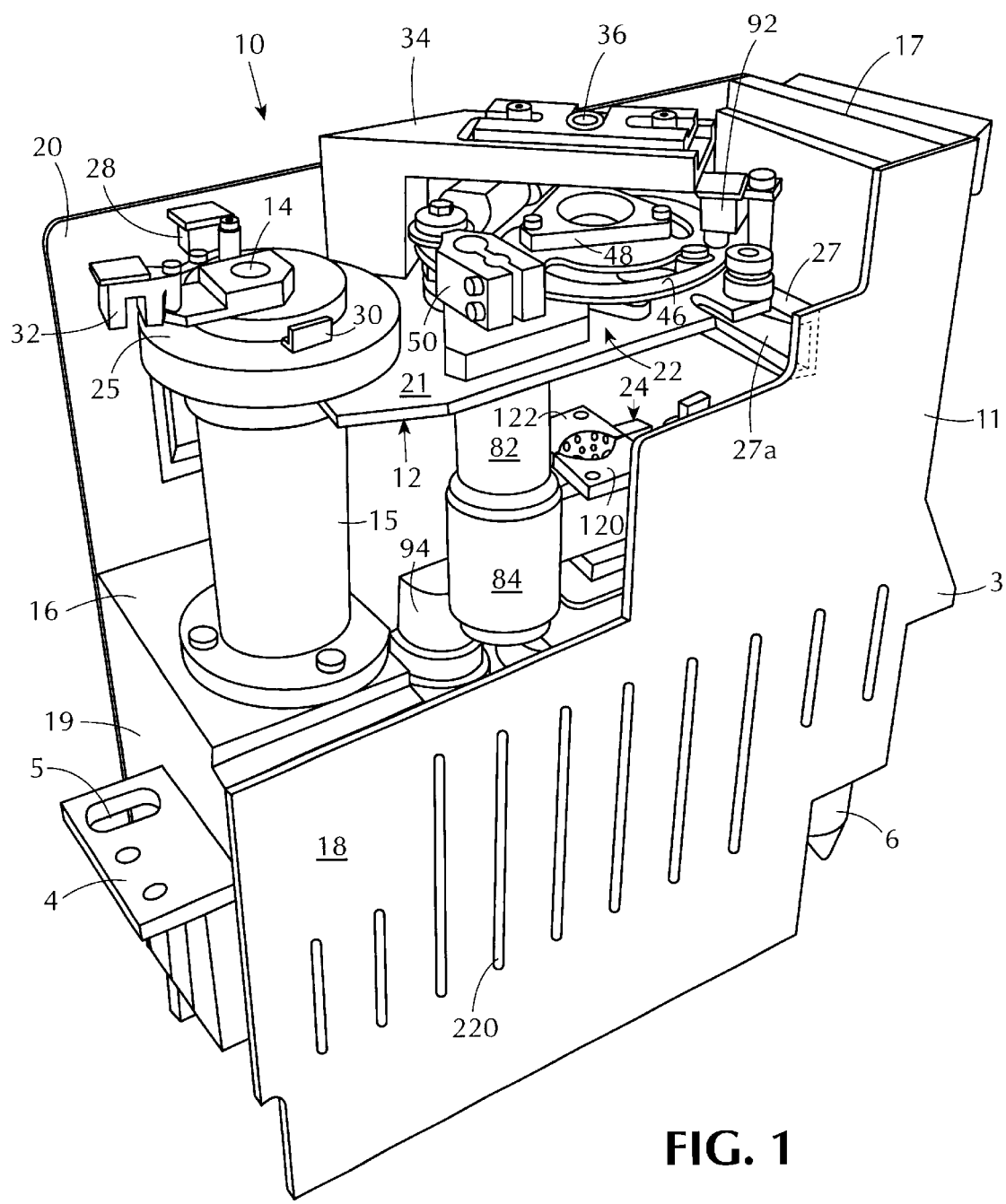
FIG. 1 is an isometric view of the decapper according to the present invention.
Figure 2:
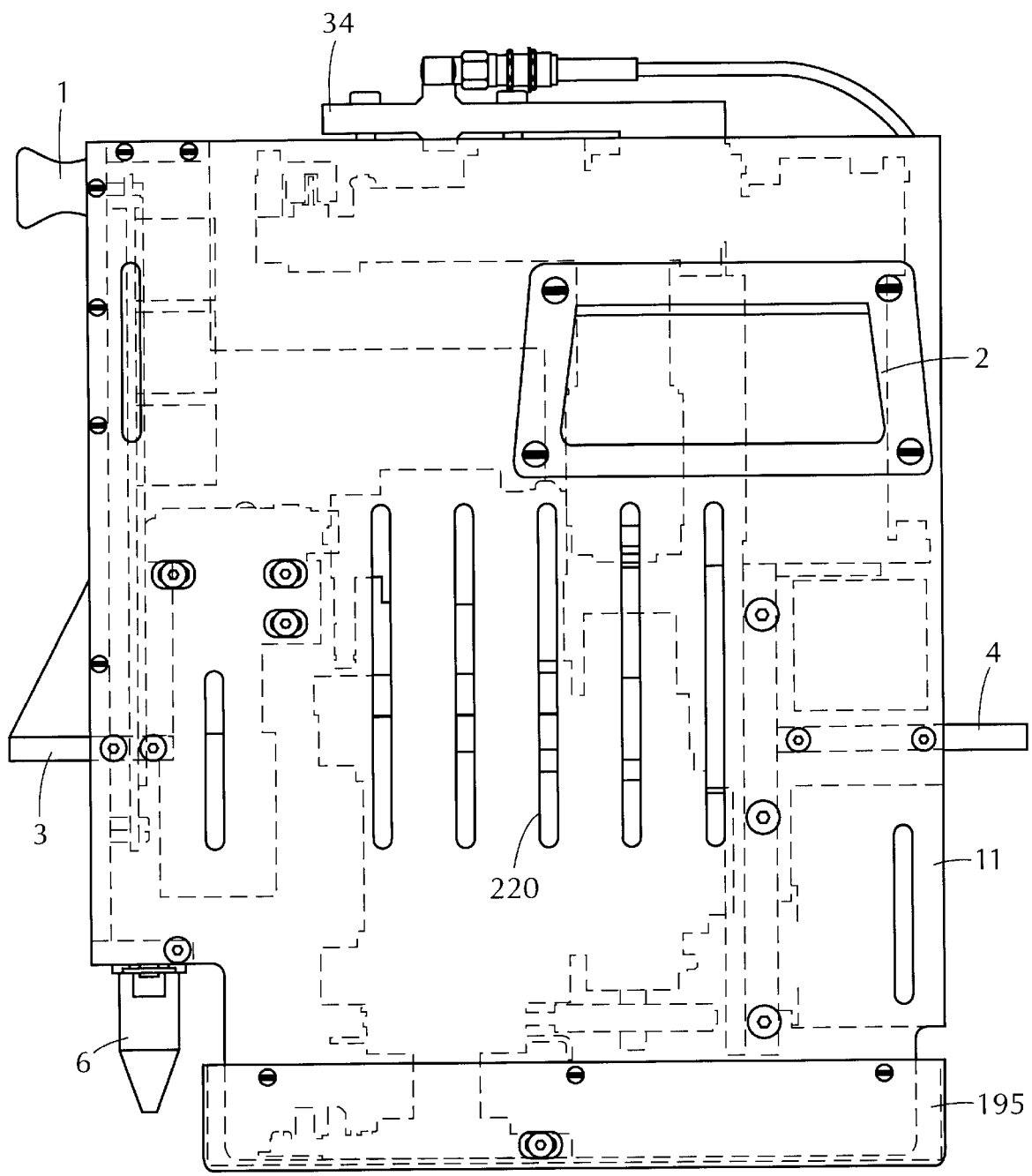
FIG. 2 is a rear view of the decapper of FIG. 1 with the various internal components illustrated in phantom.
Figure 27:
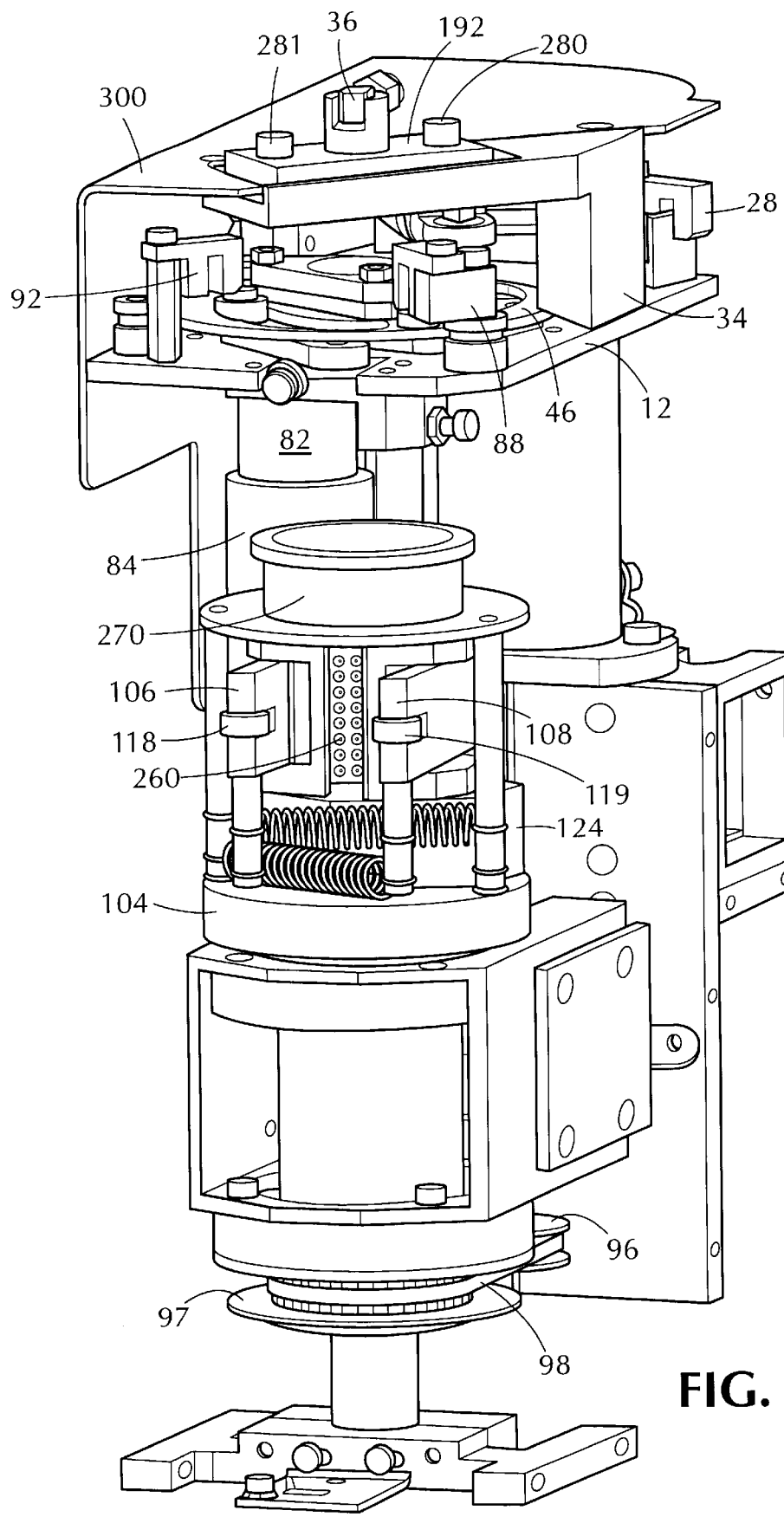
FIG. 27 is an isometric view of portions of the decapper including the decapping arm and lower grippers.
Figure 28:
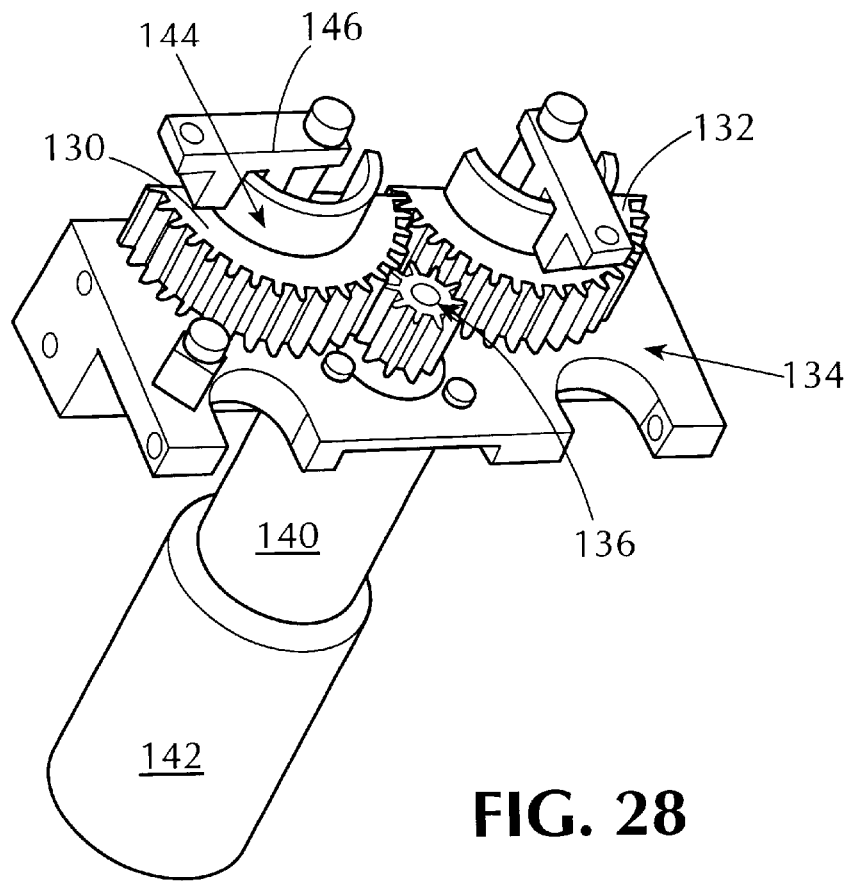
FIG. 28 is an isometric view of the subassembly used to open the lower grippers.
Figure 29:
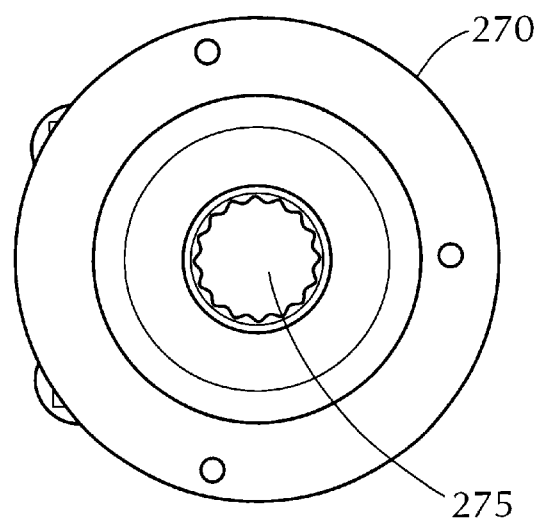
FIG. 29 is a top view of the protective cover for the lower grippers.

Referring to FIG. 1, a decapper 10 according to a preferred embodiment is designed to be compact enough to fit within an analytical instrument and preferably to form a component in a sample handler (not shown). Decapper 10 has a frame 11 comprising a front wall 18, right side wall 17, left side wall 19, and rear wall 20. Decapper 10 may be installed in the sample handler chassis (not shown) with decapper resting therein on supports 3, 4 on respective side walls 17, 19. Pins on the chassis may engage holes on supports 3, 4, such as hole 5 on support 4, and mounting pins 6 under the right side of decapper 10 to prevent frame 11 of decapper 10 from rotating. To easily clean and service decapper 10, decapper 10 is removable from the chassis where it is installed. The carrying of decapper 10 is made easier by the provision of a plurality of handles on frame 11, such as handles 1, 2. An optional L-shaped over 300 may be mounted to front wall 18 and overhang the decapper (FIG. 27). To prevent the buildup of excessive heat, slots 220 are provided in front and rear walls 18, 20 (FIGS. 1, 2).

A decapping arm 12 is pivotably coupled to a drive shaft 14 on a bidirectional DC motor (not shown), which may be coupled to a gear box to minimize the size of the required motor. The motor and gear box are encased within a steel tube 15 mounted to a support bar 16 extending between front and rear walls 18, 20. The selected combination of motor and gears should achieve a smooth, nonjerking and relatively quick motion and should be compact to fit within tube 15. An upper grippers 22 is mounted to the top of decapping arm 12 and a lower grippers 24 is mounted below upper grippers 22 to front and rear walls 18, 20. An armature 34 is also mounted to the top of plate 21 to hold an ultrasonic liquid level sensor 36 above upper grippers 22. A catch 27 is mounted between front and rear walls 18, 20 and above half-gears 130, 132.

Figure 26A:
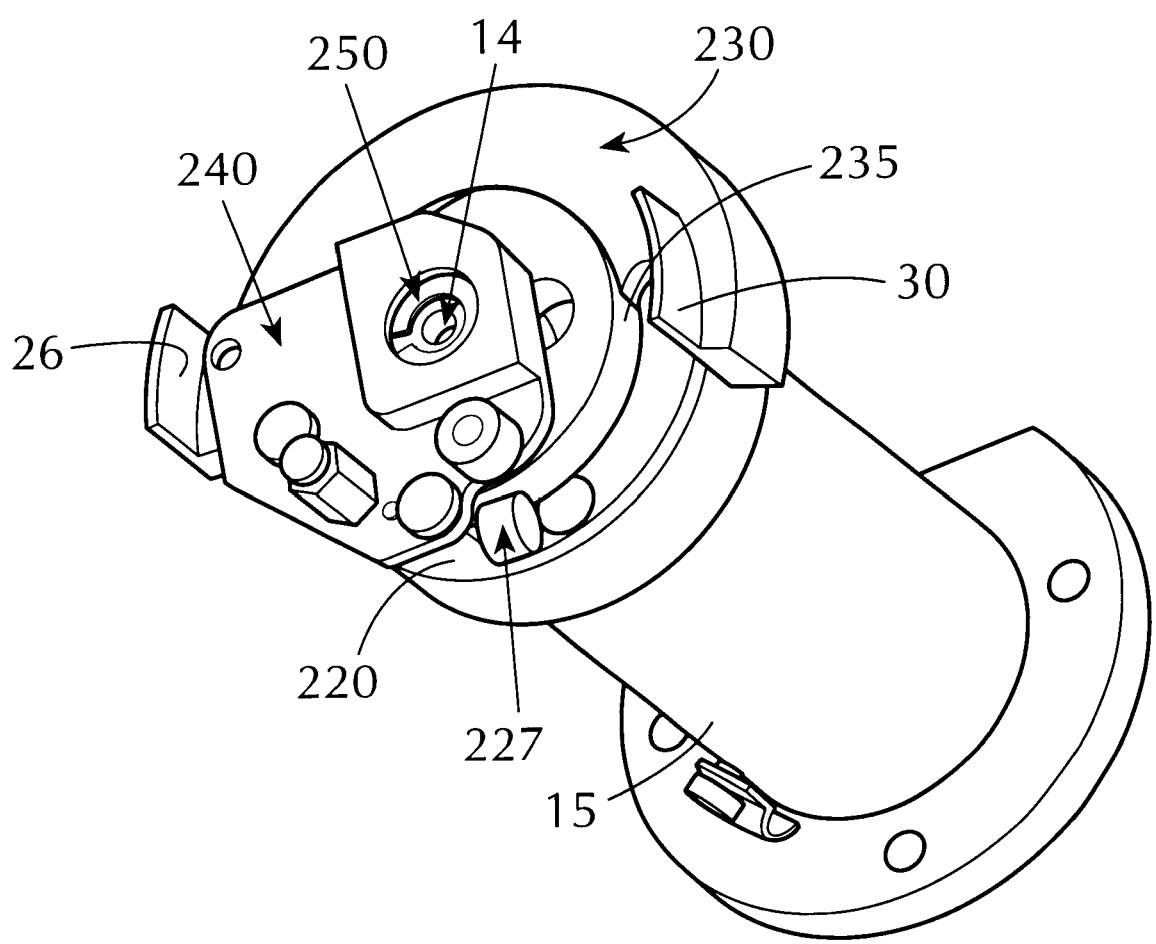
FIG. 26A is an isometric view of a modified preferred embodiment of the swing assembly for the decapping arm mounted to the steel tube housing the motor for the decapping arm.
Figure 26B:
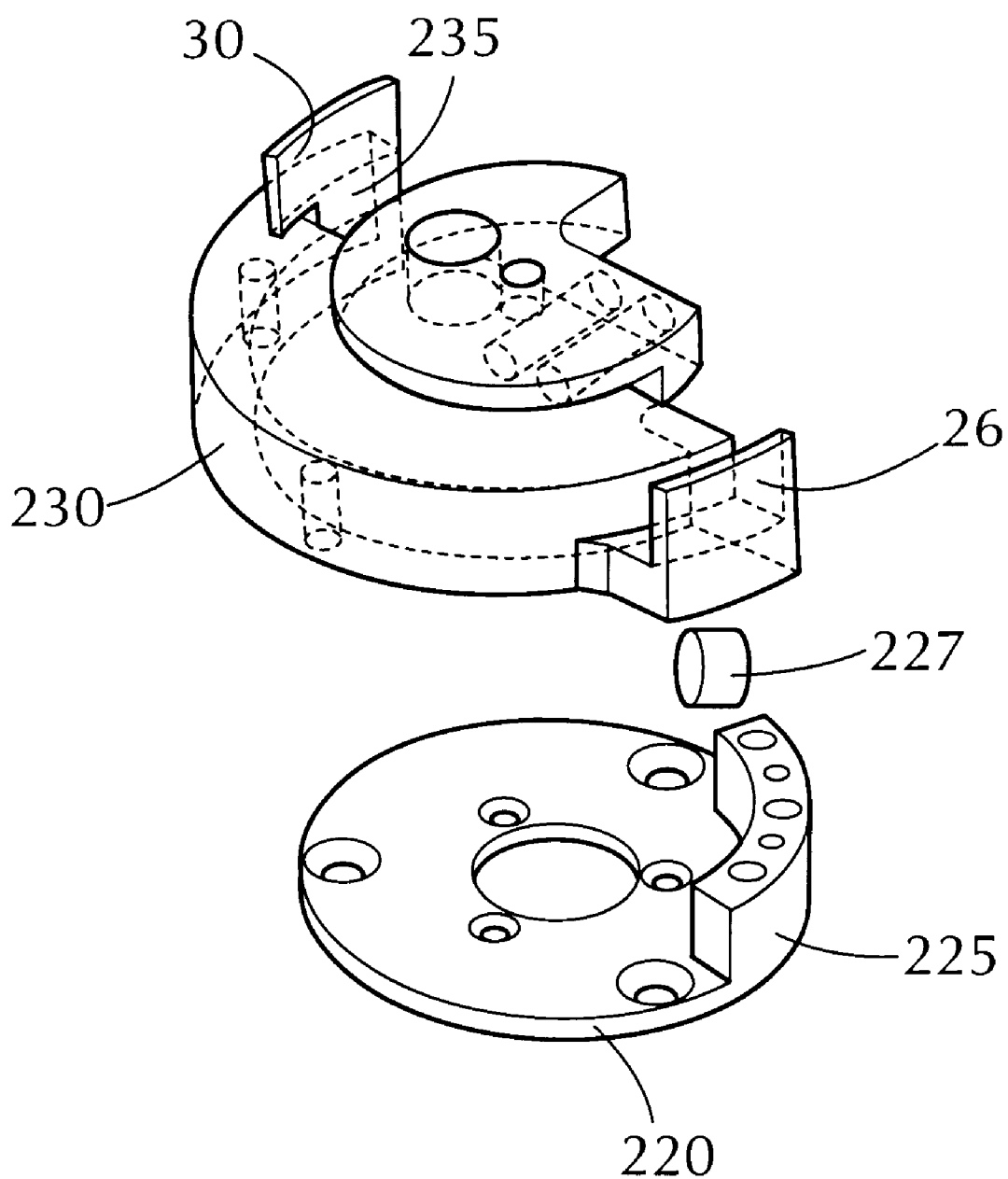
FIG. 26B is an exploded view of the socket and clamp of the modified embodiment of FIG. 26A.
Figure 30:
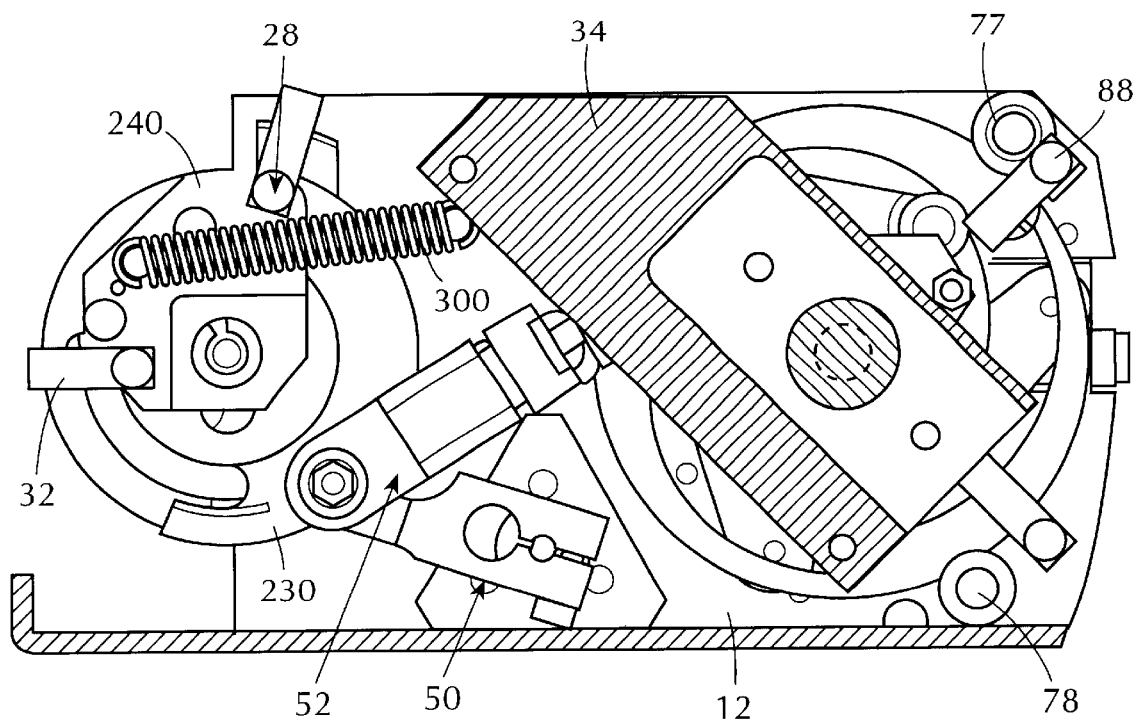
FIG. 30 is a top view of a modified decapping arm in the closed position.

Decapping arm 12 comprises a flat plate 21 mounted to a swing assembly 25, which in turn is mounted to drive shaft 14. In a preferred embodiment, illustrated in FIGS. 26A and 26B, swing assembly 25 comprises a socket 220 and clamp 230 that clamps to drive shaft 14 above socket 220 and decapping arm 12 is mounted directly to clamp 230. Socket 220 has an elevated section 225 that rises to approximately the height of clamp 230 and limits the rotation of decapping arm 12 to approximately a 90 degree rotation. A rubber stop 227 may be mounted on the side of elevated section 225 and a channel 235 may be left within clamp 230 to accommodate stop 227. A stationary end plate 240 is mounted above clamp 230 with ball bearings 250 surrounding drive shaft 14. End plate 240 serves as a mounting point on decapping arm 12 for an optional torsion spring 300 (FIG. 30) to bias decapping arm 12 in a closed position when the decapper is powered down so decapping arm 12 does not swing open when the decapper is removed from the instrument. The other mounting point for torsion spring 300 is elsewhere on a movable portion of decapping arm 12.

Several of FIGS. 1–25 illustrate an alternate embodiment of swing assembly 25 in which swing assembly 25 comprises a circular plate. The below description describes the decapper with the swing assembly 25 shown in FIG. 26A.

In FIG. 1, decapping arm 12 is shown in a closed (or "decap") position wherein upper grippers 22 are located above lower grippers 24. In this position, decapping arm 12 is supported on the left side by tube 15 and on the right side of decapper 10 by a roller follower 29 mounted to the right side of decapping arm 12 that rides up along a ramp section of channel 27a in catch 27 and cams within catch 27 (FIGS. 1, 3, 4B and 5). Roller 29 engages the bottom of channel 27a toward the front, wider section of channel 27a. When a cap is removed from a test tube by pulling the test tube away from the cap as described below, roller 29 exerts a force against the bottom of channel 27a and thereby prevents the right side of decapping arm 12 from being pulled downward. When the cap finally separates from the test tube, roller 29 exerts a force against the top of channel 27a and thereby prevents decapping arm 12 from momentarily snapping upward. Thus, the cam on the right side of decapping arm 12 prevents decapping arm 12 from becoming deformed due to upward and downward forces during decapping. A metal rod 23, also mounted to the right side of decapping arm 12, contacts hard stop 27b, which may be a rubber pad, on the back of catch 27 and extends lengthwise in channel 27a when decapping arm 12 is in the closed position.

Figure 3:
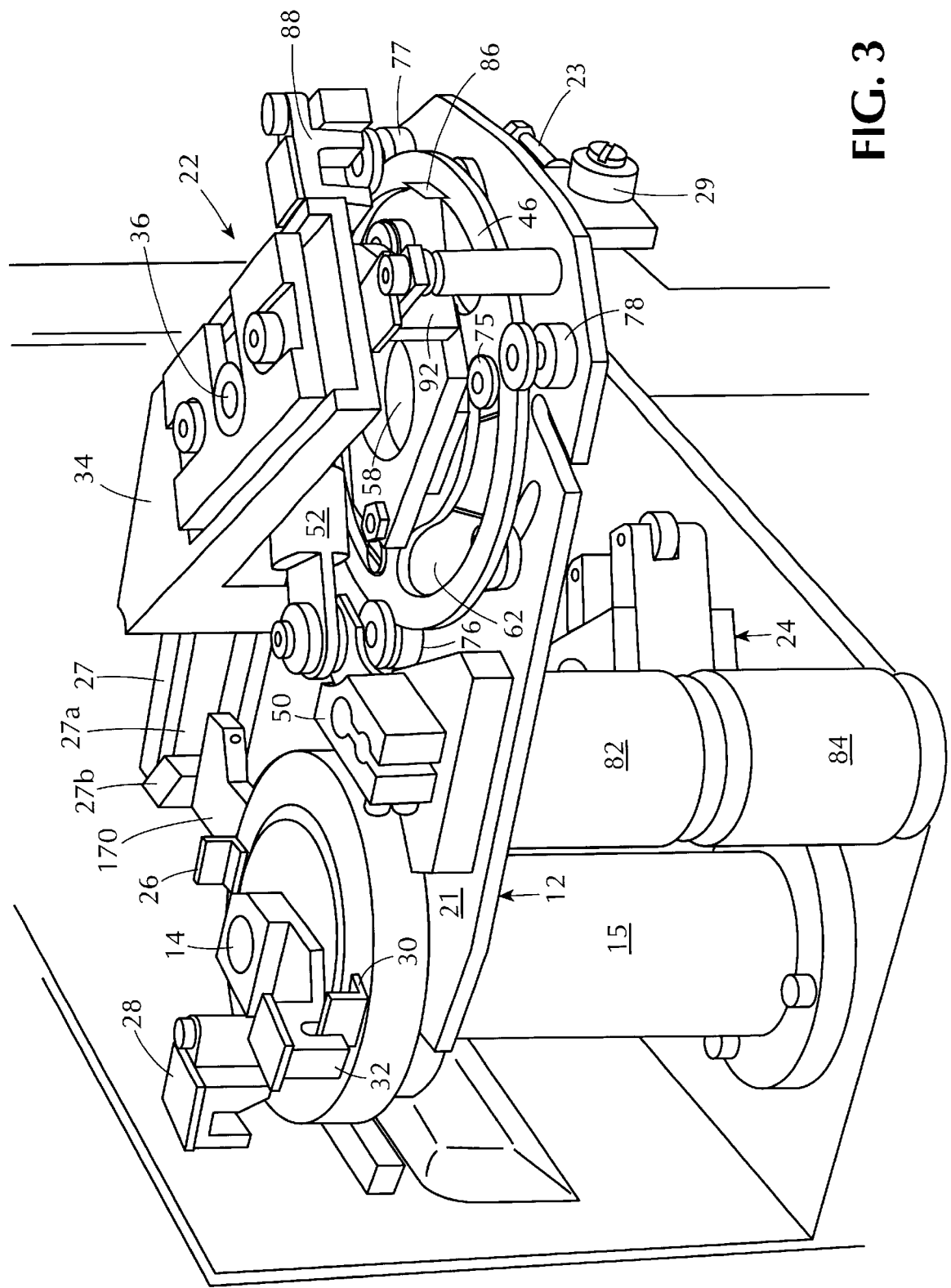
FIG. 3 is an isometric view of the decapping arm on the decapper pivoted to a first position where a test tube may be inserted into or removed from the decapper.

Decapping arm 12 is rotatable from the closed position to an open (or "waste") position shown in FIG. 3 by rotating decapping arm 12 ninety (90) degrees about shaft 14 to be perpendicular lengthwise to front and rear walls 18, 20. This causes upper grippers 22 to move as well to a position beyond front wall 18 rather than above lower grippers 24. The rotation of decapping arm 12 is driven by the aforementioned DC motor.

To confirm when decapping arm 12 is in the closed position as in FIG. 1, a first flag 26 is mounted on clamp 220 and is positioned to enter sensor 28, which is preferably a hall effect sensor. As decapping arm 12 is moved to the open position, flag 26 rotates with clamp 220 out of sensor 28 and a second flag 30 on clamp 220 rotates into a second sensor 32, which is similar to sensor 28, when decapping arm 12 is in the open position, to provide a signal that decapping arm 12 is in the open position. As either of flags 26 and 30 enter the respective sensors 28 and 32, the motor for decapping arm 12 slows to bring decapping arm 12 into the fully closed or open positions. Decapping arm 12 is held in the closed position with rod 23 against stop 27b and is held in the open position with clamp 220 against stop 227 by pulse width modulation to apply incremental pulses to hold decapping arm 12 in the desired position.

Figure 4A:
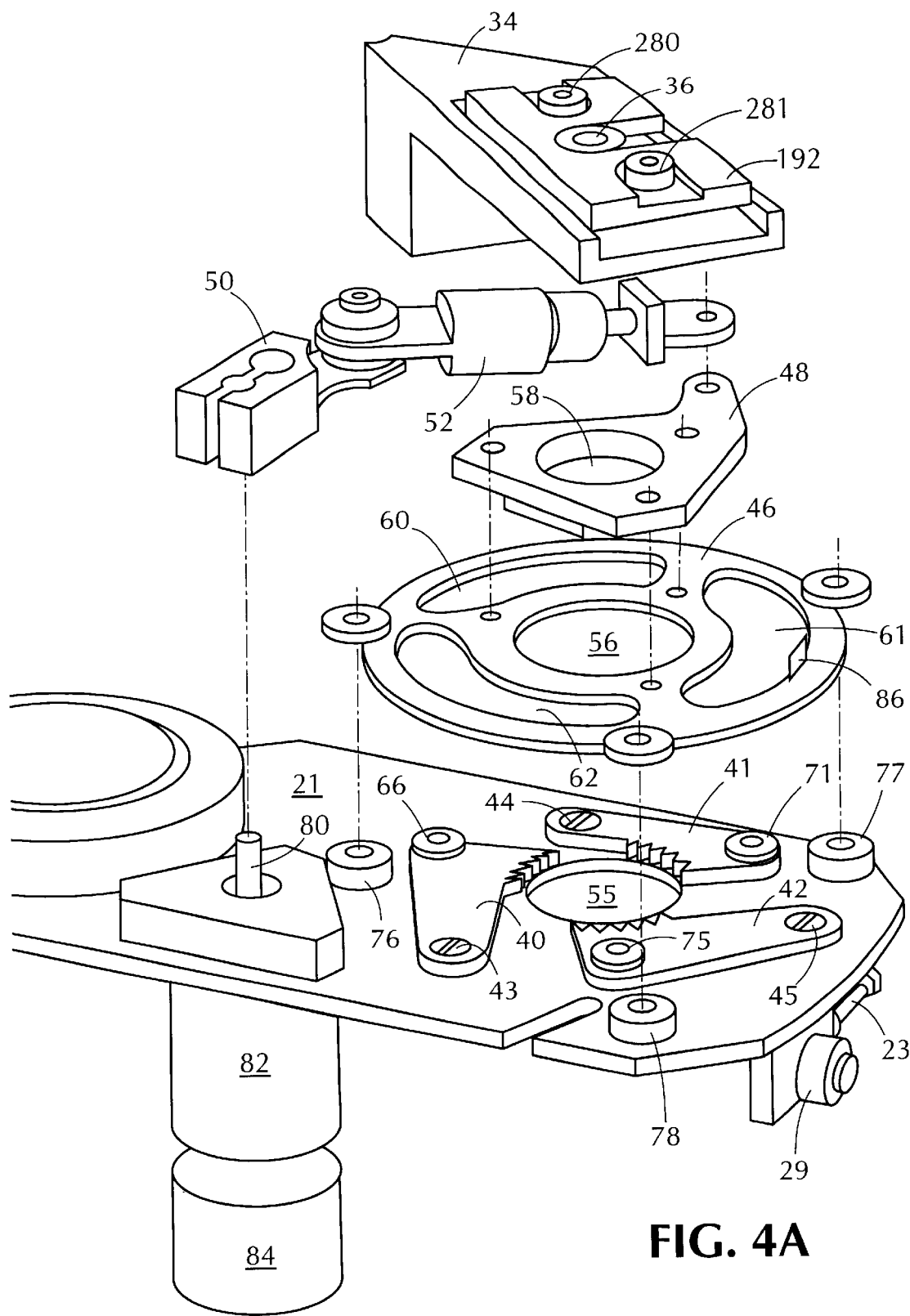
FIG. 4A is an exploded view of the upper grippers which are mounted to the decapping arm.
Figure 4B:
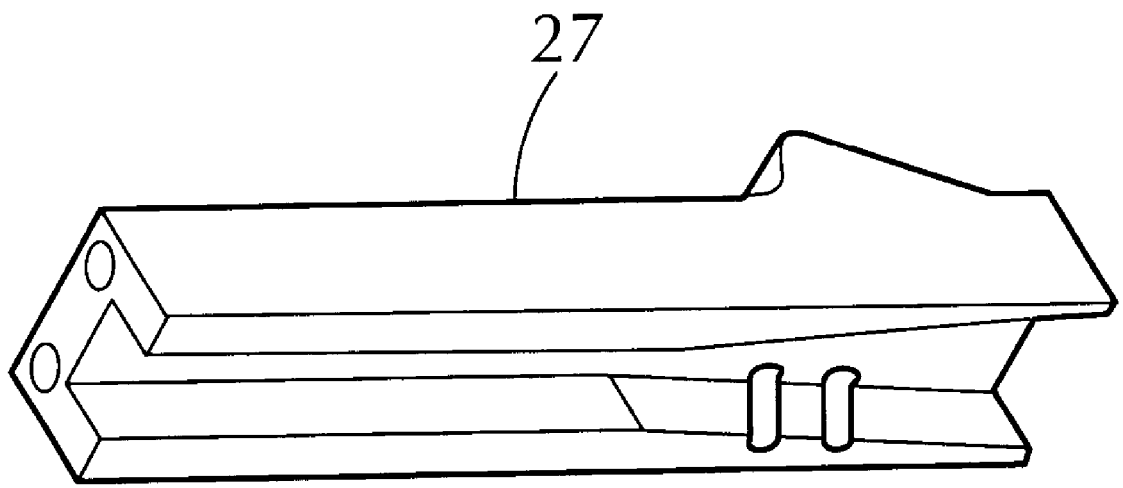
FIG. 4B is an isometric view of the catch in which the decapping arm cams upon closing.
Figure 6:
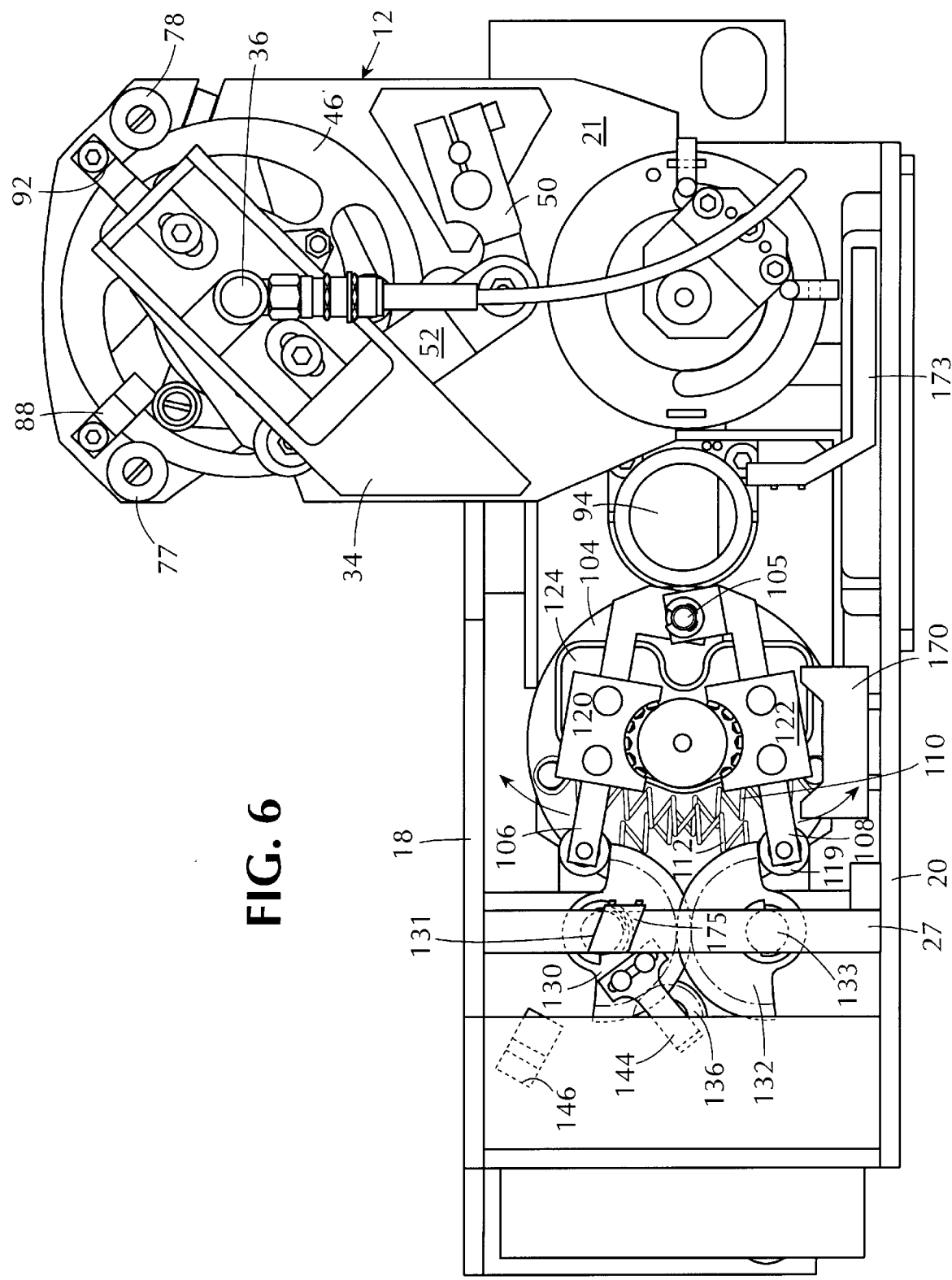
FIG. 6 is a top view of the decapper as shown in FIG. 5 but with half-gears pushing open right and left lever arms of the lower grippers.
Figure 7:
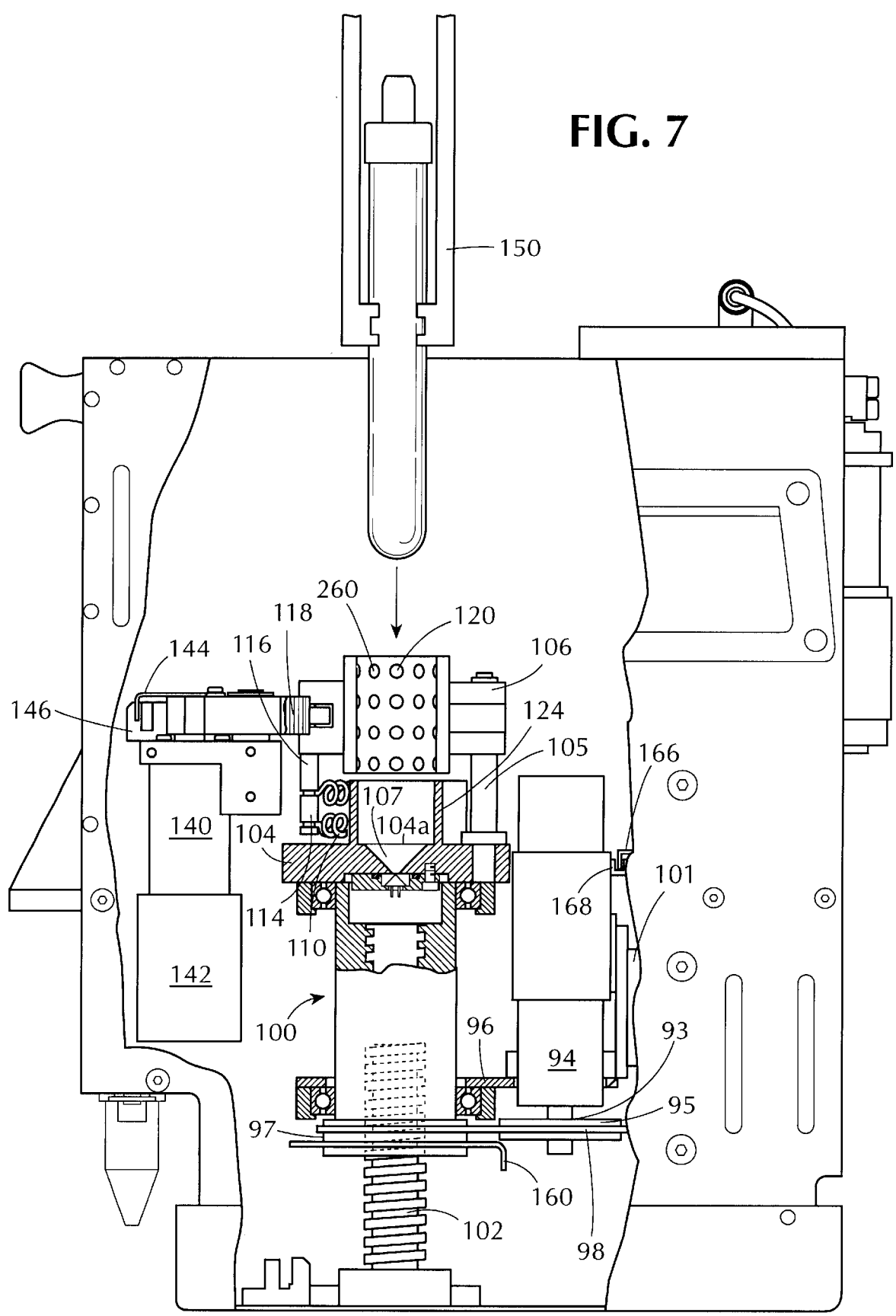
FIG. 7 is a rear, cutaway view of the decapper showing fingers on a robotic arm transporting a test tube to be deposited into the lower grippers (left lever arm is not shown)

Upper grippers 22 is shown in greater detail in the exploded view of FIG. 4A. Upper grippers 22 comprises three identical horizontal jaws 40–42 pivotably mounted to plate 21 at points 43–45, respectively, a rotatable wheel 46 which is coupled to jaws 40–42, a plate 48 mounted to the top of wheel 46, a rotatable arm 50, and a linkage 52 between arm 50 and plate 48. Jaws 40–42 are shown in FIG. 4A pivoted to an open position with teeth on each of jaws 40–42 recessed behind aperture 55 in plate 21 of decapping arm 12. Wheel 46 and plate 48 have apertures 56, 58, respectively, that are aligned above aperture 55 to provide clearance for a raised portion of a cap on a test tube. Apertures 55, 56, 58 are also aligned under sensor 36 for sensor 36 to read the liquid level of a test tube in lower grippers 24 aligned under apertures 55, 56, 58.

Wheel 46 is rotatably mounted with bearings to locate wheel 46 slightly above jaws 40–42 so as not to interfere with the movement of the jaws. Bearings may consist of three equally spaced steel roller bearings 76–78 mounted to plate 21 on decapping arm 12 around the circumference of wheel 46. Wheel 46 has three arcuate slots 60–62. Jaws 40–42 are coupled to slots 60–62 on wheel 46 with respective roller followers 66, 71, 75. Slots 60–62 have a cam profile to cause roller followers 66, 71, 75 to translate jaws 40–42 so that the teeth thereon move inward above aperture 55 to grip a cap.

Arm 50 is clamped to a drive shaft 80 extending from gear box 82, which is coupled to a bidirectional DC motor 84. The rotation of drive shaft 80 causes arm 50 to pivot and push or pull linkage 52, as appropriate, which in turn causes wheel 46 to rotate. When wheel 46 is rotated fully clockwise, jaws 40–42 are in their recessed positions, as shown in FIG. 4. This is detected by a flag 86 on wheel 46 that enters a sensor 88, preferably a hall effect sensor, mounted to decapping arm 12 and overhanging wheel 46. When motor 84 is activated to turn arm 50 counterclockwise, wheel 46 is rotated in a counterclockwise direction as well and jaws 40–42 are rotated inward with teeth on jaws 40–42 positioned above aperture 55, as in FIG. 16. Flag 86 rotates with wheel 46 to enter sensor 92, also preferably a hall effect sensor, mounted to decapping arm 12 when wheel 46 is fully turned. A bracket 96 is mounted to a rail 99 with a bearing block 101 (FIG. 8), the particular bearing block being selected to minimize noise generated by travel of rotatable assembly 100 along rail 99.

Lower grippers 24 comprise a rotatable assembly 100 that moves up and down along lead screw 102 by activation of a motor 94 mounted adjacent rotatable assembly 100. (FIG. 7) Motor 94 is coupled to rotatable assembly 100 with a pulley 95 mounted to a shaft 93 on motor 94 which drives a timing belt 98 coupled to a circular section 97 having teeth on the bottom of rotatable assembly 100. Lead screw 102 is preferably threaded with a 4 mm pitch, which is the same pitch as the threading used on test tubes from most manufacturers (including Sarstedt and Braun) for twist-on caps. As a result, a single rotation of rotatable assembly 100 will unscrew screw-on caps from test tubes.

Figure 31:
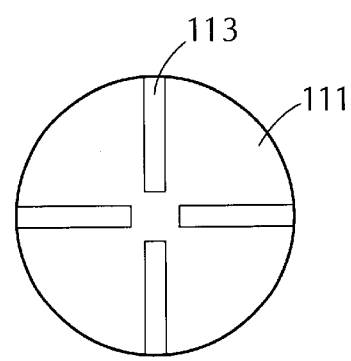
FIG. 31 is a top view of a plate that sits in the base of the rotatable assembly of the lower grippers.

Rotatable assembly 100 functions as a test tube holder having a base 104. The top of base 104 has a void 107 in the center of base 104 and a plate 111, having holes 113 through which liquid may pass, sits above void 107. (FIG. 31) Rotatable assembly 100 comprises two lever arms 106, 108 mounted to a shaft 105 mounted to base 104. Lever arms 106, 108 both pivot about shaft 105 and are spring-loaded with springs 110, 112, respectively, mounted to respective mounts 114, 116 into a closed position such that lever arms 106, 108 are essentially parallel to each other. This prevents the dropping of a test tube which is held between lever arms 106, 108 in the event of a power outage. A rubber pad 120, 122 with a high friction inner surface to grip test tubes securely is mounted to each of respective lever arms 106, 108. The high friction surface preferably has knobs 260 (FIG. 27) to grip the test tube securely even if there is liquid on the exterior of the test tube. A roller 118, 119 is mounted at the end of each respective lever arm 106, 108.

Should a test tube break within decapper 10 or spill some of its contents, a U-shaped reservoir 124 that has an outer wall and an open top is formed on the top of base 104 and at least under the location where test tubes are to be held between lever arms 106, 108. Reservoir 124 should be large enough to hold the entire liquid sample of the largest test tube that may be placed in decapper 10. Liquid passes through holes 113 in plate 111 and into void 107 that forms a smaller reservoir in base 104 where liquid is detected by a sensor 199.

Two half-gears 130, 132 are mounted to pivot points 131, 133, respectively, on a fixed horizontal surface 134 that extends between front and rear walls 18, 20 to the right of rotatable assembly 100. Gears 130, 132 have teeth along the semi-circles 130a, 132a that defines the half-gears and have smooth edges 130b, 132b along the back of half-gears 130, 132. A pinion 136 is mounted to a drive shaft 138 of a motor 142 and gear box 140 mounted beneath half-gears 130, 132.

Figure 9:
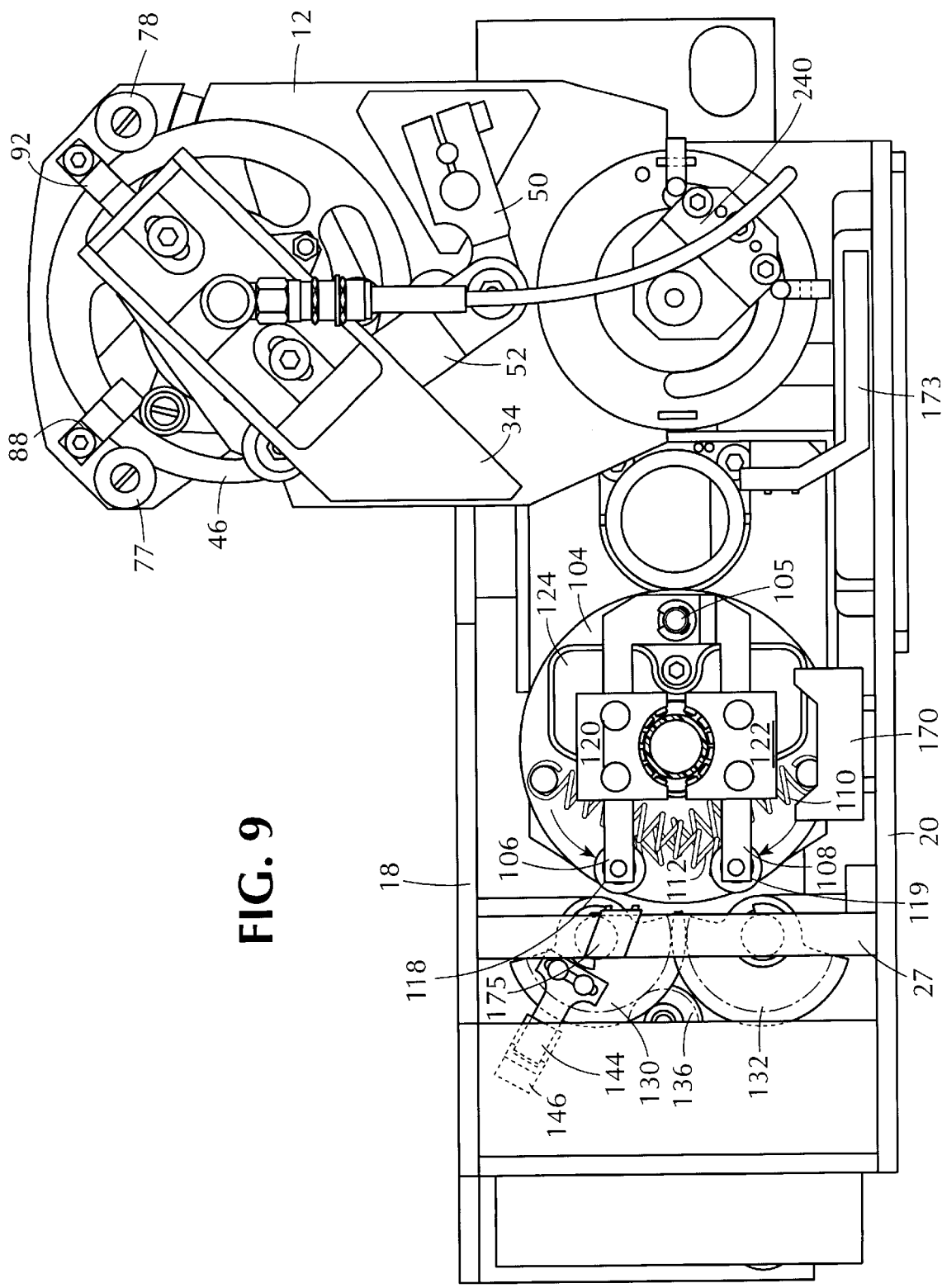
FIG. 9 is a top view of the decapper after a test tube has been inserted in the lower grippers and the lever arms have been released to grip the test tube (the decapping arm is shown pivoted to the first position)

In their initial retracted position, half-gears 130, 132 are rotated as shown in FIG. 9 so as not to be in contact with lever arms 106, 108 should lever arms 106, 108 be adjacent half-gears 130, 132. A semicircular flag 144 on gear 130 triggers a hall effect sensor 146 mounted adjacent pinion 136 when gears 130, 132 are fully retracted. To limit the distance to which lever arms 106, 108 may be opened, a semicircular flag 145 on gear 132 passes through hall-effect sensor 147 when gears 130, 132 are retracted and, as flag 145 exits from sensor 147, motor 142 is stopped.

As stated above, the decapper according the present invention is designed to be an integral component within a sample handler of an automated instrument for decapping capped test tubes. Alternatively, it may be operated as a decapping station along a lab automation transport line, such as the LabCell transport line manufactured by the Bayer Corporation. In either of these two possibilities, a robotic arm (not entirely shown) may transport and insert individual test tubes into decapper 10 for decapping. One such robotic arm is described in the referenced Robotics application. Fingers 150 grip the test tube during transport. (Of course, decapper 10 could also be a stand-alone component into which capped test tubes are manually inserted for decapping, although this is not the preferred embodiment.)

Decapper 10 is preferably controlled by an external controller, such as a controller based on the Intel 386EX microprocessor, which activates the motors for decapping arm 12, upper grippers 22, rotatable assembly 100 for lower grippers 24 and pinion 136, and communicates with the various sensors and motors on decapper 10 via an RS232 port which may be located on the right side of decapper 10 between mounting pins 6. The decapper design of the preferred embodiment is particularly desirable where the sample handler has only a narrow space in which to mount decapper 12.

Figure 8:
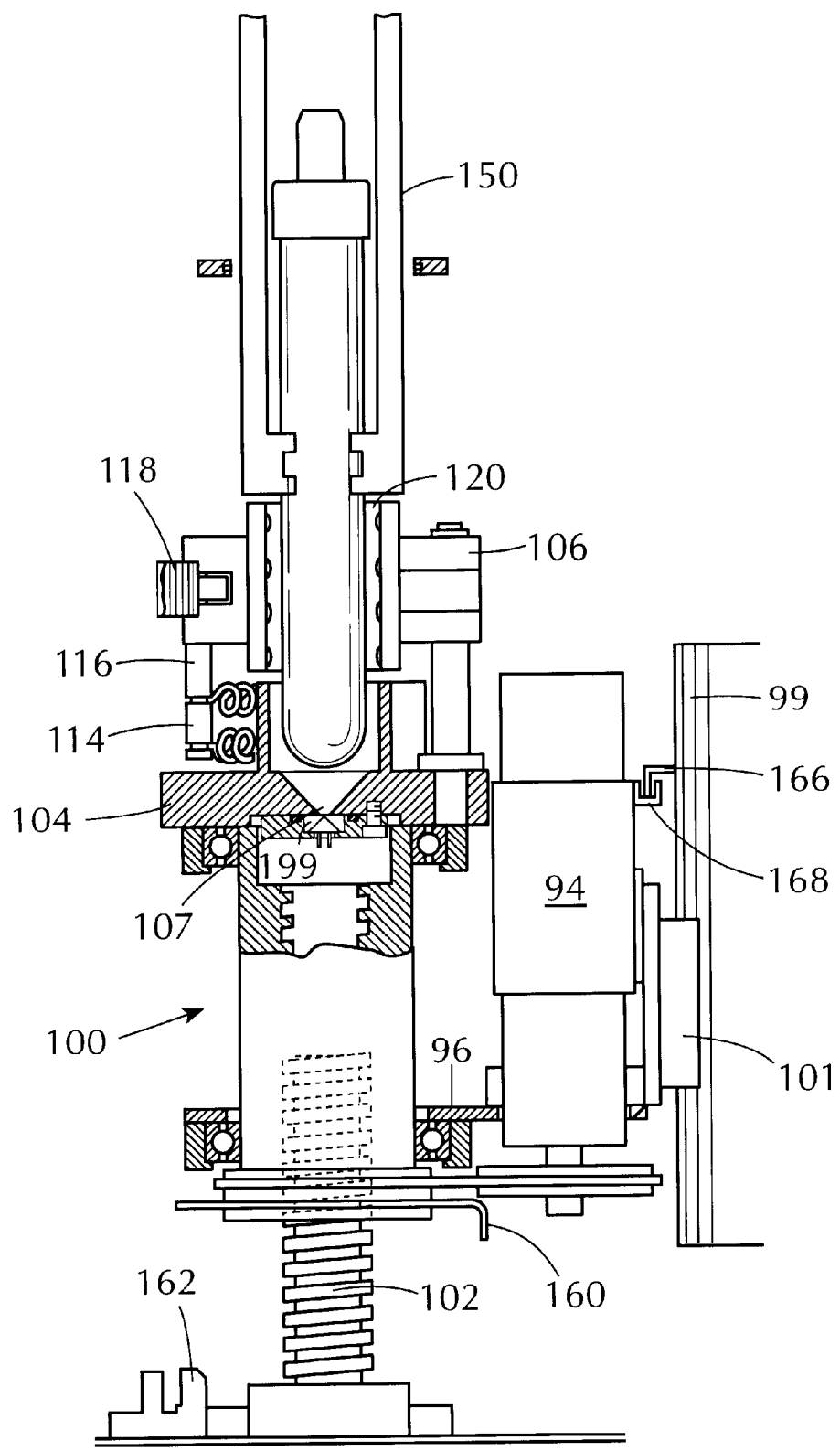
FIG. 8 is a rear view of the lower grippers with the test tube of FIG. 7 deposited into the lower grippers while the fingers of the robotic arm continue to grip the test tube.

In operation, when a capped test tube is to be decapped, that test tube is transported to decapper 10, such as with the robotic arm. Initially, when not in use, decapping arm 12 is either in the open or closed positions, rotatable assembly 100 is fully lowered along lead screw 102 (with flag 160 passing within sensor 162), and lever arms 106, 108 are closed. In preparation for the arrival of the test tube, decapping arm 12 is moved to its open position, if it is not already open, to expose lower grippers 24. At the same time, rotatable assembly 100 of lower grippers 24, including base 104 and lever arms 106, 108, is rotated counterclockwise to move upward along lead screw 102 by activation of motor 94 and travels along rail 99 until lever arms 106, 108 are positioned at the same height as half-gears 130, 132 and are pointing toward right wall 17 of decapper 10. (FIG. 5) The vertical position of half-gears 130, 132 is programmed into the workstation software and tracked by a built-in homing mechanism and encoder for rotatable assembly 100 so the rotatable assembly 100 may be properly positioned. Before lever arms 106, 108 are opened, the proper positioning of rotatable assembly 100 is confirmed by a flag 168 on bracket 96 triggering a hall effect sensor 166 mounted along rail 99. (FIG. 8)

When sensor 166 is triggered, motor 142 may be activated by the sample handler controller to rotate pinion 136 in a clockwise direction. The rotation of pinion 136 causes gear 130 to rotate in a counterclockwise direction and the rotation of gear 130 drives gear 132 to rotate clockwise. As gears 130, 132 rotate, smooth edges 130b, 132b of gears 130, 132 push against rollers 118 and 119 on respective lever arms 106, 108, thereby pushing lever arms 106, 108 apart from one another against the force of springs 110 and 112. (FIG.

6) The test tube, held between fingers 150 on the robotic arm, is then be inserted between rubber pads 120, 122 (FIG. 7) and lowered with fingers 150 until the test tube is fully seated on plate 111 on base 104. (FIG. 8) The sample handler controller is preferably programmed to know the precise horizontal location on decapper 10 into which a test tube should be placed and how far the test tube held by the robotic arm must be lowered. An inertia switch (not shown) may be included on the robotic arm to stop the robotic arm if it detects that the test tube has been lowered too far and hit base 104 or any other element of decapper 10.

The distance from the top of rubber pads 120, 122 on lever arms 106, 108 to the top of base 104 of rotatable assembly 100 in which the test tube sits is maintained to be a smaller distance than the height of the test tube located beneath the bottom of fingers 150 so that fingers do not interfere with the operation of lower grippers 24. The robotic arm should preferably always pick up the test tubes a set distance from the bottom of the test tube so that test tubes of various heights may be inserted into and decapped by decapper 10 without interfering with fingers 150. Decapper 10 should be configured to at least accommodate the tallest commonly-used test tube having the tallest cap.

Figure 10:
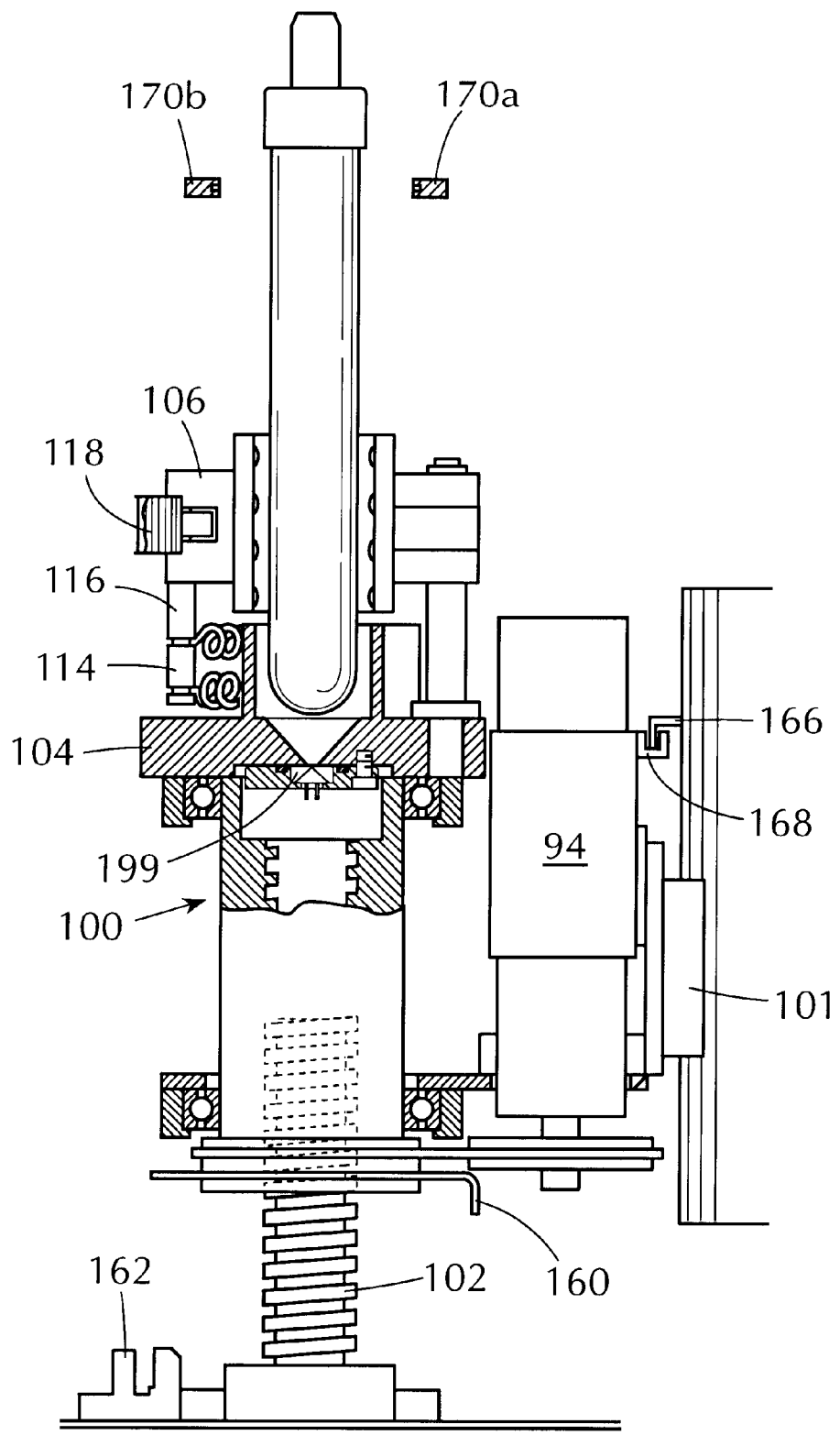
FIG. 10 is a partial rear view of the decapper in the vicinity of the lower grippers with the lower grippers raised along lead screw and a portion of the housing around the lead screw cutaway.
Figure 11:
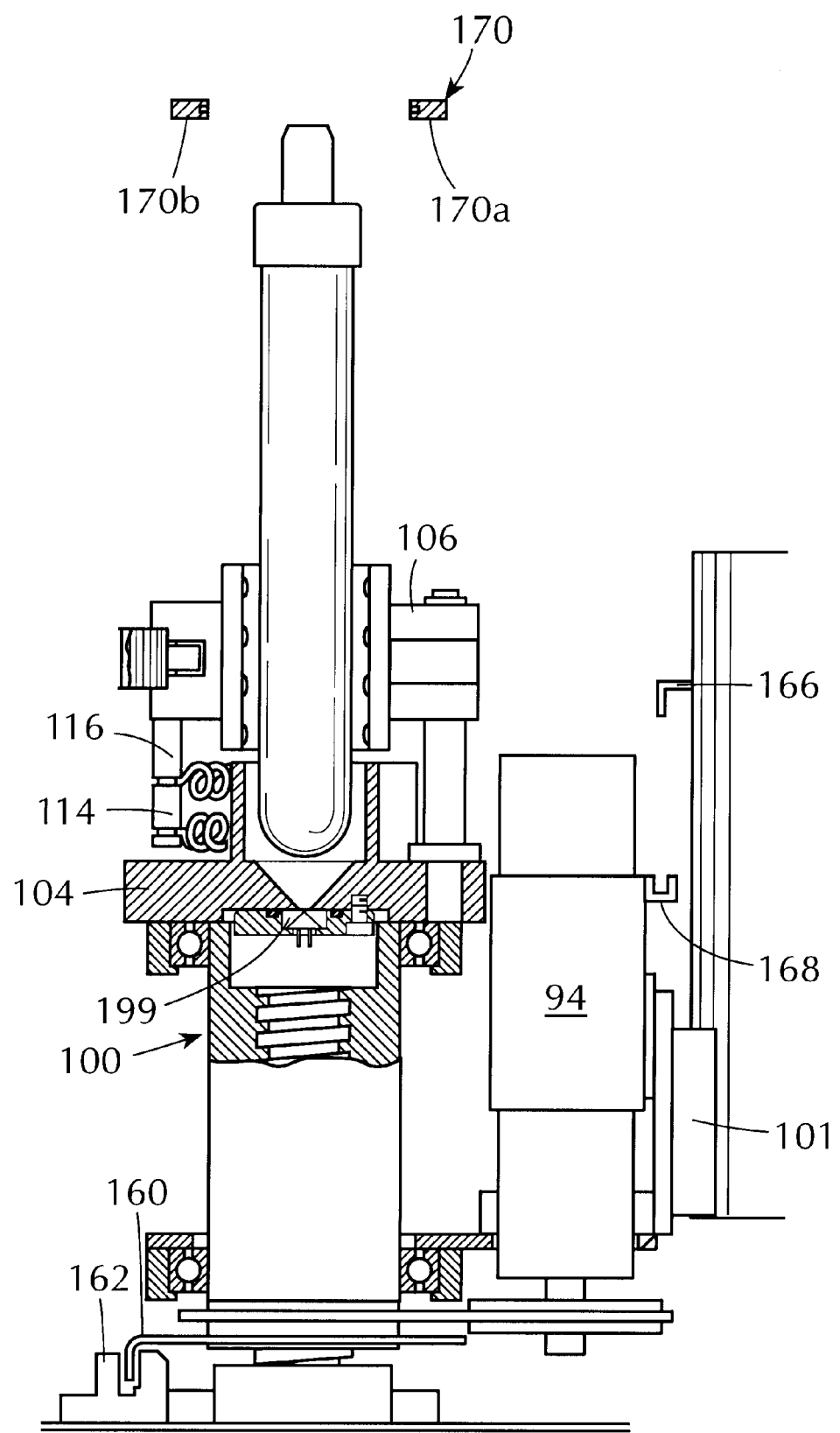
FIG. 11 is a partial rear view of the decapper shown in FIG. 10 but with lower rippers rotated fully downward along the lead screw.
Figure 12:
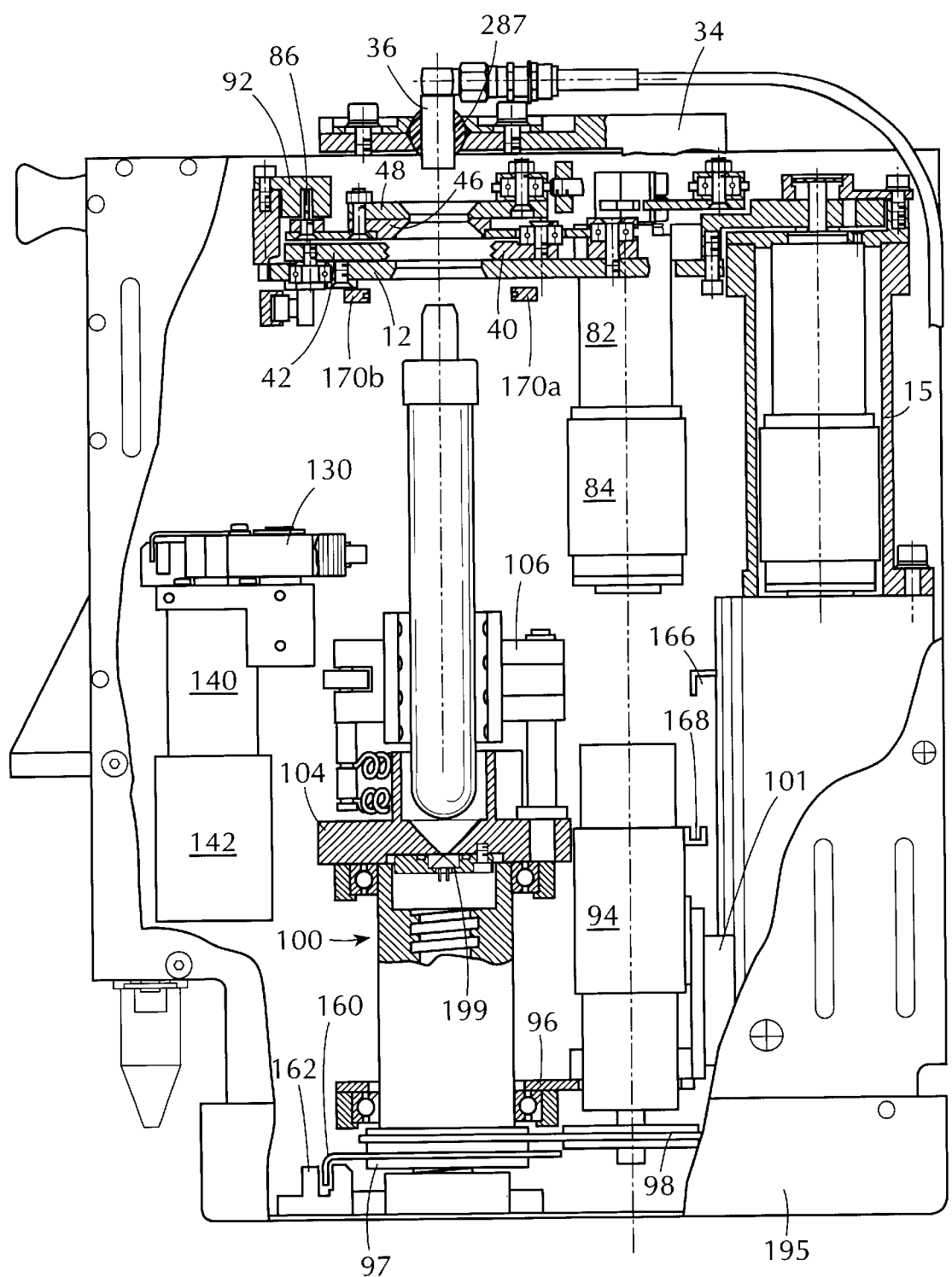
FIG. 12 is a rear view of the decapper with a portion of the outer housing of the decapper and the housing around the lead screw cutaway and the decapping arm in a second position pivoted above the lower grippers.
Figure 13:
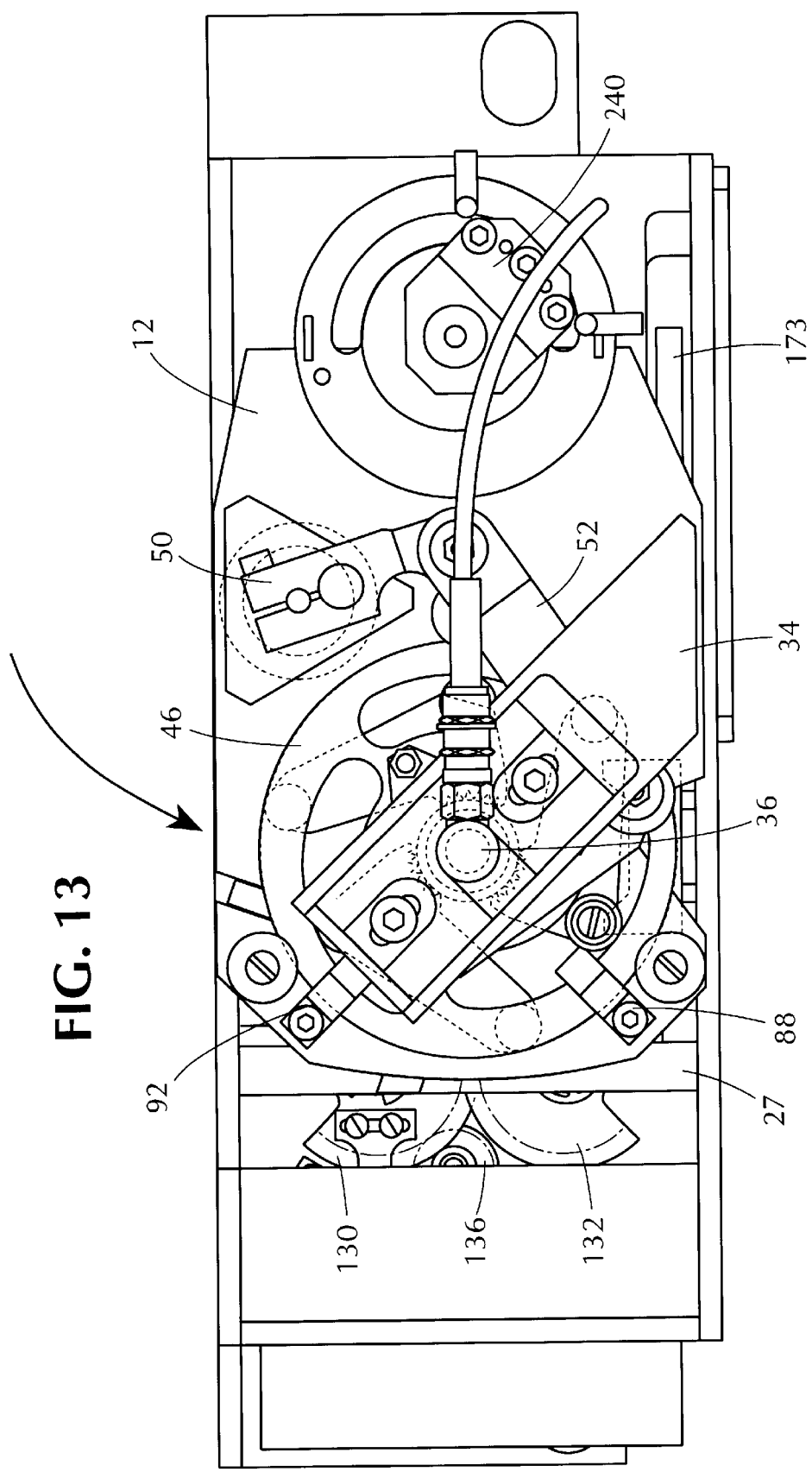
FIG. 13 is a top view of the decapper with the decapping arm in the second position.

Once the robotic arm has fully lowered the test tube, as indicated by a handshake from the robotic arm to the sample handler controller, motor 140 is activated in the reverse direction to cause pinion 136 to rotate counterclockwise, thereby causing gear 130 to rotate clockwise and gear 132 to rotate counterclockwise until flag 144 enters sensor 146. This releases lever arms 106, 108 gradually to firmly hold the test tube. Fingers 150 on the robotic arm may then release the test tube and are removed from decapper 10. (FIG. 10)

Figure 14:
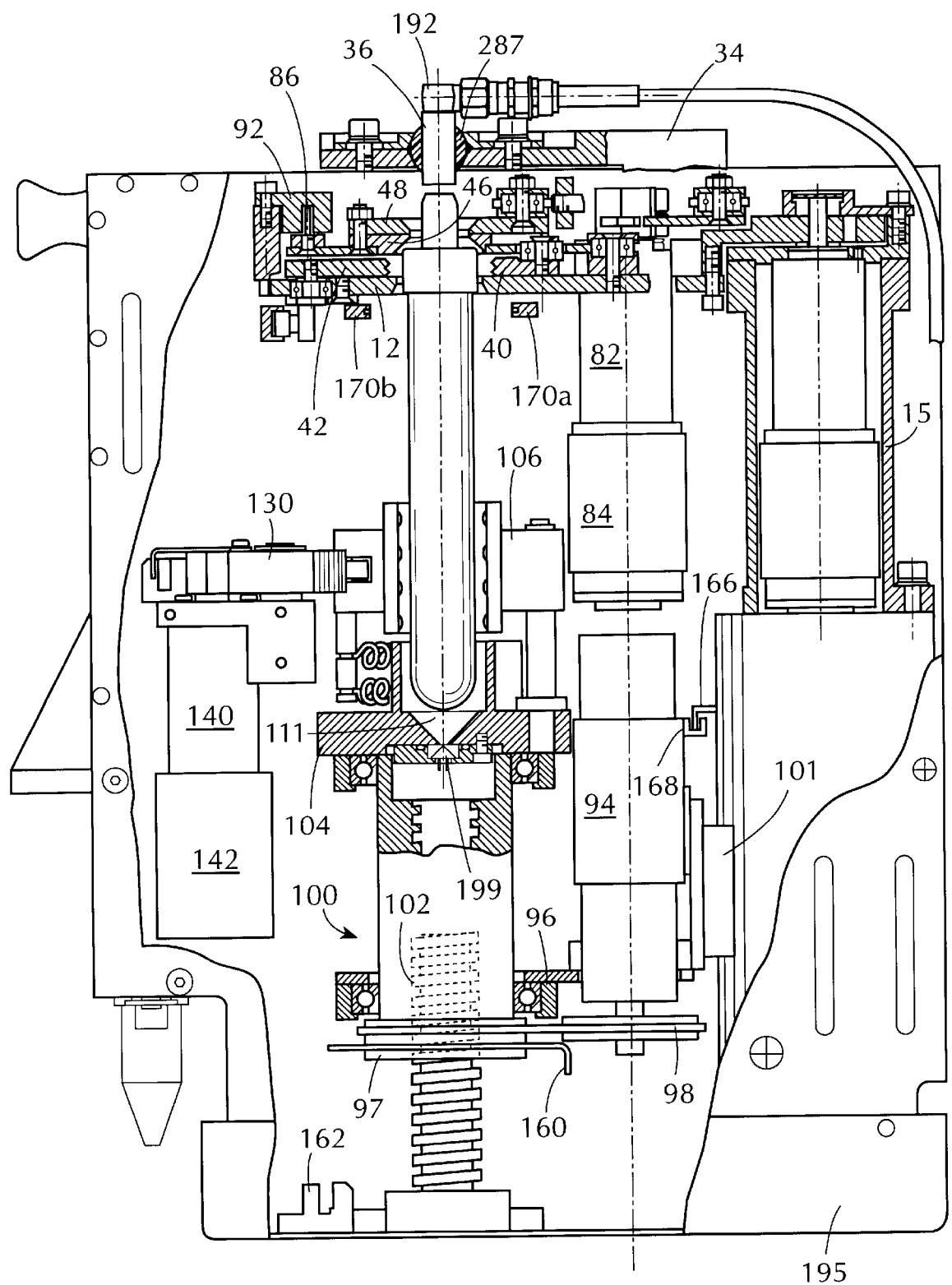
FIG. 14 is a rear view of the decapper with a portion of the outer housing of the decapper and the housing around the lead screw cutaway, the decapping arm in a second position pivoted above the lower grippers, and the lower grippers raised along lead screw to the position wherein the test tube is raised to place the cap within the upper grippers.

After the test tube is firmly gripped by pads 120, 122, on lower grippers 24, motor 94 is activated to lower the rotatable assembly 100 until the upper edge of the test tube in lower grippers 24 is beneath the level of an infrared sensor 170 having a transmitter 170a and receiver 170b mounted within a bracket having the illustrated shape. Sensor 170 is thus used as a "tube sensor" with receiver 170b detecting reflections from the outer surface of the test tube from the infrared beam from transmitter 170a until the tube is lowered beneath the level of sensor 170. (FIGS. 11 and 12) Lowering rotatable assembly 100 provides clearance for decapping arm 12, which swings back to the closed position after a tube is lowered beneath sensor 170. (FIG. 13) After the decapping arm 12 is in the closed position, rotatable assembly 100 with the test tube held therein then rotates upwards until the top of the cap of the test tube is detected by sensor 170, after which rotatable assembly 100 rotates a fixed number of turns, based on the height of the cap, as determined by sensor 174 as explained below, and motor 94 is then turned off. This leaves the cap within aperture 55 on plate 21 of the decapping arm, aperture 56 of wheel 46 and aperture 58 where it is stopped near the tapered circumference of aperture 58 (FIG. 14). Apertures 55 and 56 are tapered inward with an increasing elevation to accommodate the various shapes of available caps. These apertures and aperture 58 allow caps with a raised central portion (such as the illustrated cap which is representative of the caps on test tubes made by Sarstedt of Germany) to be removed by this decapper as well. An outward taper in aperture 58 accommodates a nipple on the side of some Sarstedt caps.

Two parallel sensors 172, 174 ("cap sensors"), preferably infrared sensors, are mounted in a bracket 173 at a level above the level of sensor 170, each comprising a transmitter 172a, 174a, mounted adjacent motor 15, and a receiver 172b, 174b, mounted in a bracket 175 to the top of catch 27 to face transmitters 172a, 174a. Transmitter 172a is aligned to transmit a beam diagonally through the center of the axis centered within pads 120, 122B to detect caps with a raised central portion. If the test tube is capped, the cap will block the beam of sensor 172. If it is not capped, the beam will pass from transmitter 172a to receiver 172b uninterrupted. Sensor 174 is positioned approximately 6 mm away from sensor 172 and is used to detect a cap with a raised portion that is not centered on the cap. The cap information from sensors 172 and 174 is used to determine the type of cap and how many times rotatable assembly 100 must be rotated to raise the cap within upper grippers 22. Sensors 170, 174 will also detect whether a test tube without a cap was inserted into the decapper by mistake so that the uncapped test tube is not crushed by jaws 40–42 as they close to grip a cap of a test tube during the decapping process.

Figure 15:
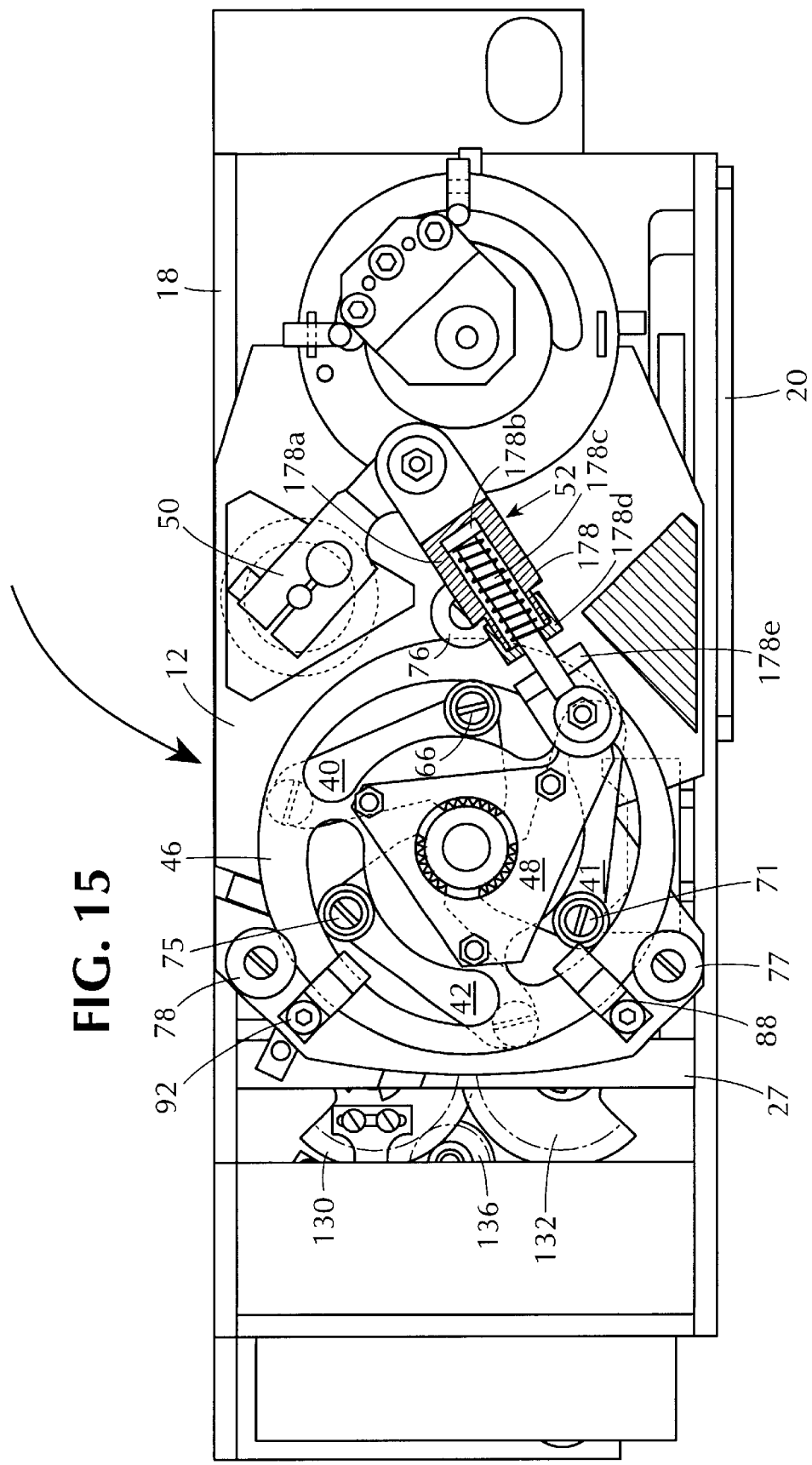
FIG. 15 is a top view of the decapper with the decapping arm in the second position, the ultrasonic liquid level sensor and sensor holder removed, and the linkage for opening and closing the upper grippers shown in cutaway.
Figure 16:
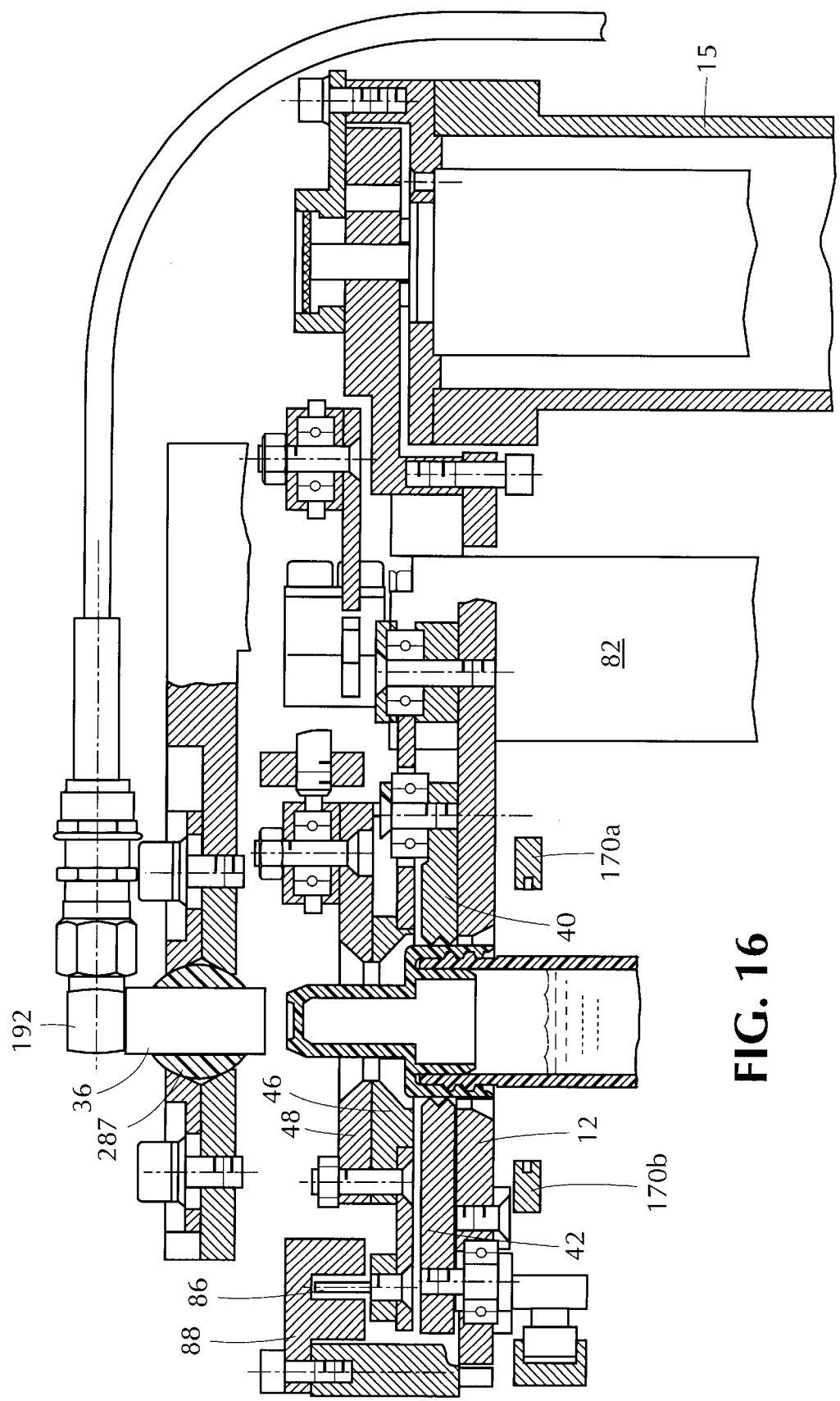
FIG. 16 is a rear, cutaway view of the upper portion of the decapper.
Figure 17:
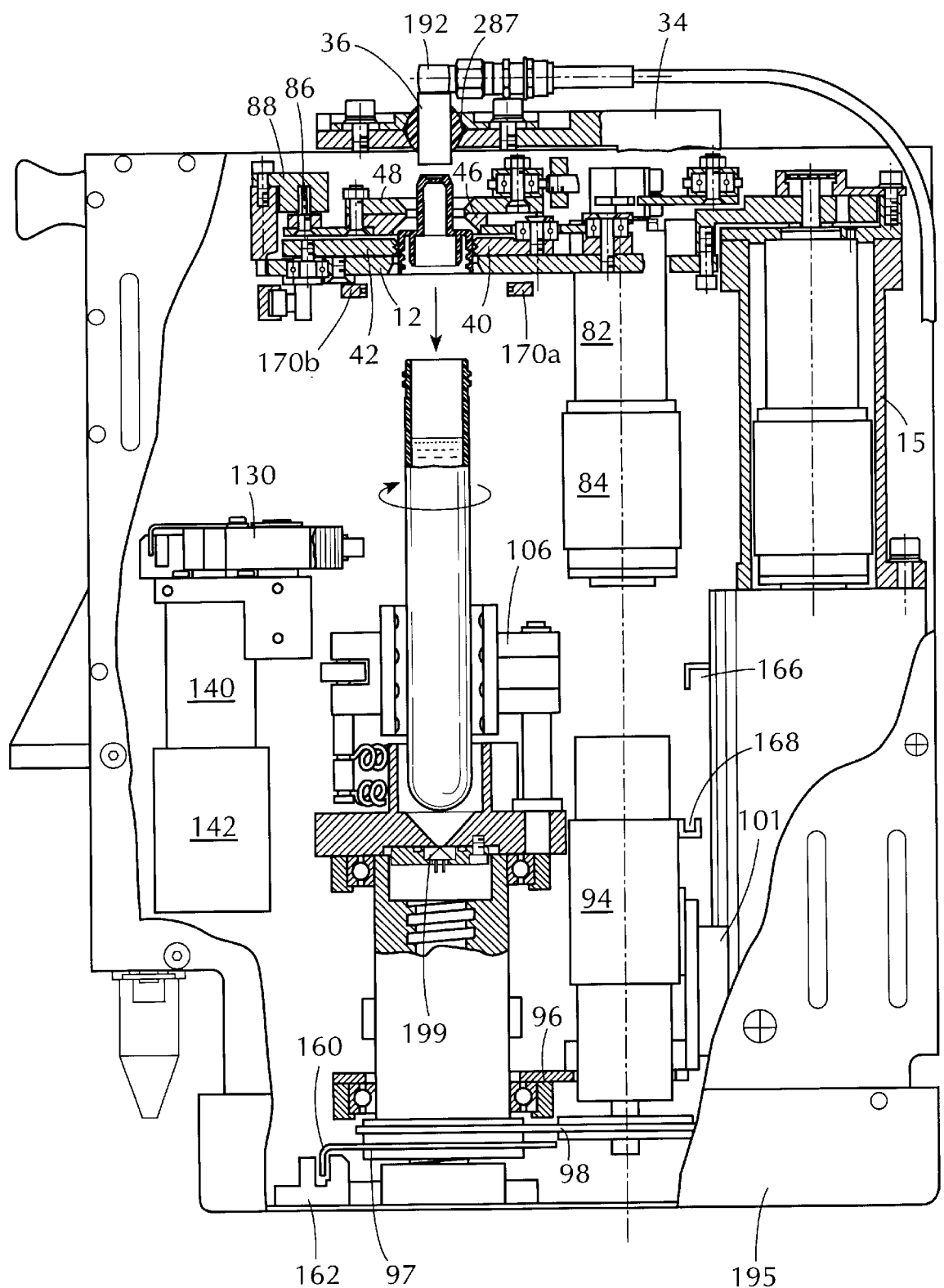
FIG. 17 is a rear, cutaway view as in FIG. 14 but after the upper grippers have gripped the cap and the lower grippers with the test tube have been rotated fully downward to remove the cap.

After the cap is positioned within upper grippers 22, motor 84 is activated and rotates arm 50 counterclockwise, thereby pulling linkage 52 and causing wheel 46 to rotate counterclockwise. (FIGS. 15 and 16) This closes jaws 40–42 around the cap and holds the cap in place. Wheel 46 is prevented from fully turning by the engagement of jaws 40–40 against the cap. Motor 84, which is a servo motor, stops when it encounters the counteracting force on arm 50 generated when jaws 40–42 engage the cap.

Where plastic gears are used in gear box 82, linkage 52 preferably comprises a spring-loaded cylinder 178a, a piston 178b placed within cylinder 178a, a torsion spring 178c, a socket 178d to hold spring within cylinder 178a and an eye 178e. Using the spring-loaded 178a linkage 52 prevents linkage 52 from breaking as arm 50 causes jaws 40–42 to close against the cap by absorbing excess torque by temporarily compressing spring 178a. (FIG. 15)

Figure 18:
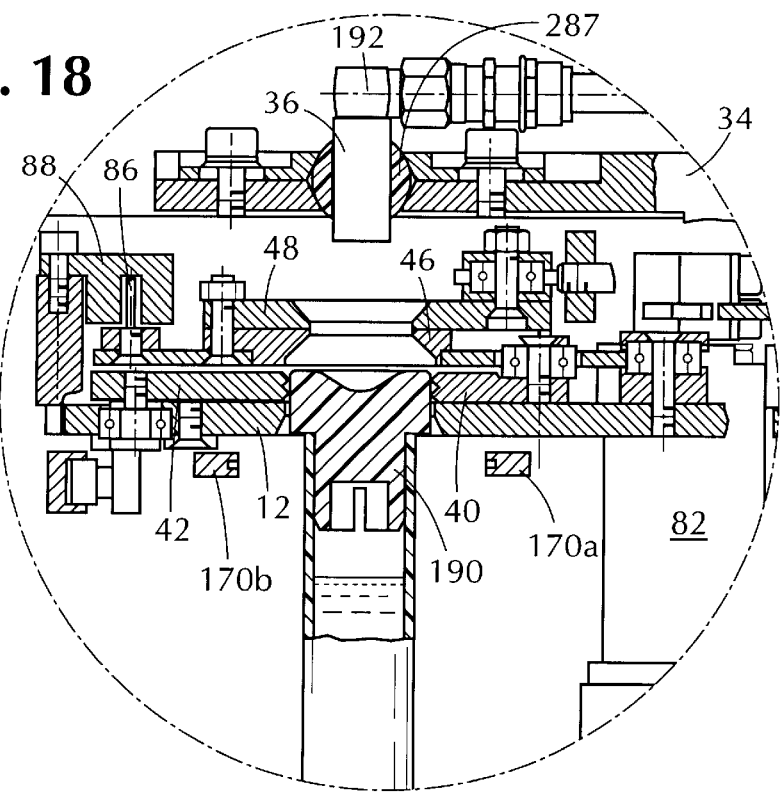
FIG. 18 is a rear, cutaway view of the upper grippers as in FIG. 16 but with the grippers gripping a rubber stopper cap instead of the twist-off cap illustrated in FIG. 14.
Figure 19:
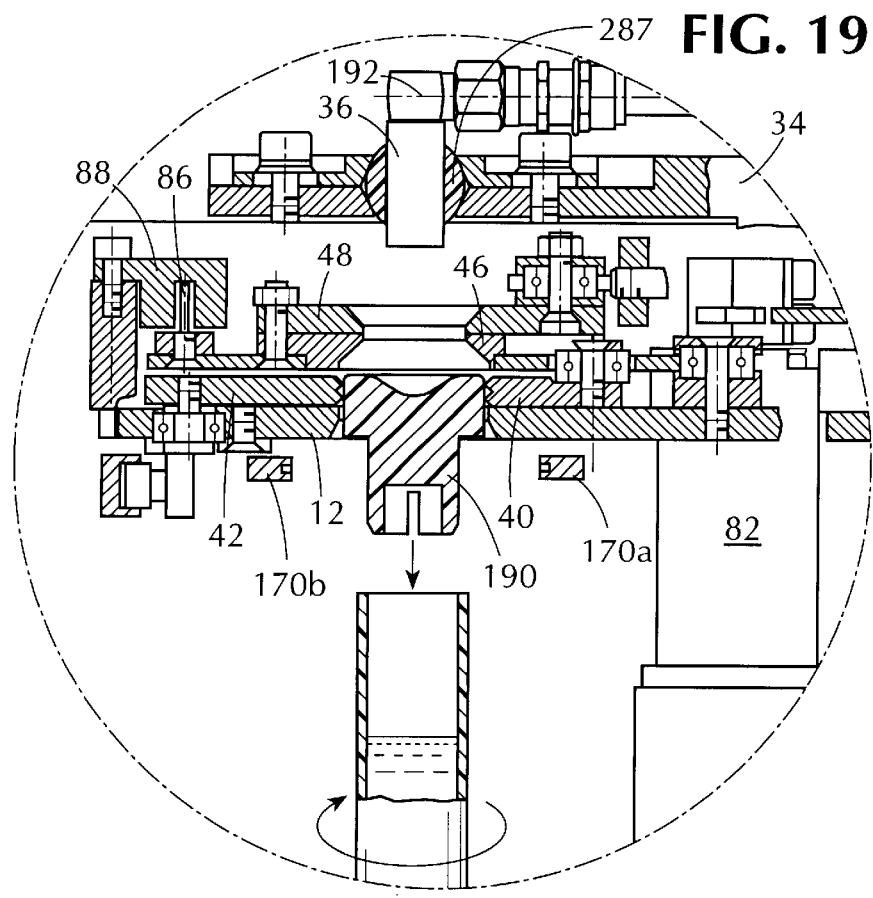
FIG. 19 is rear, cutaway view of the upper grippers gripping the rubber stopper cap of FIG. 18 but after the lower grippers have been rotated downward to remove the cap.
Figure 20:
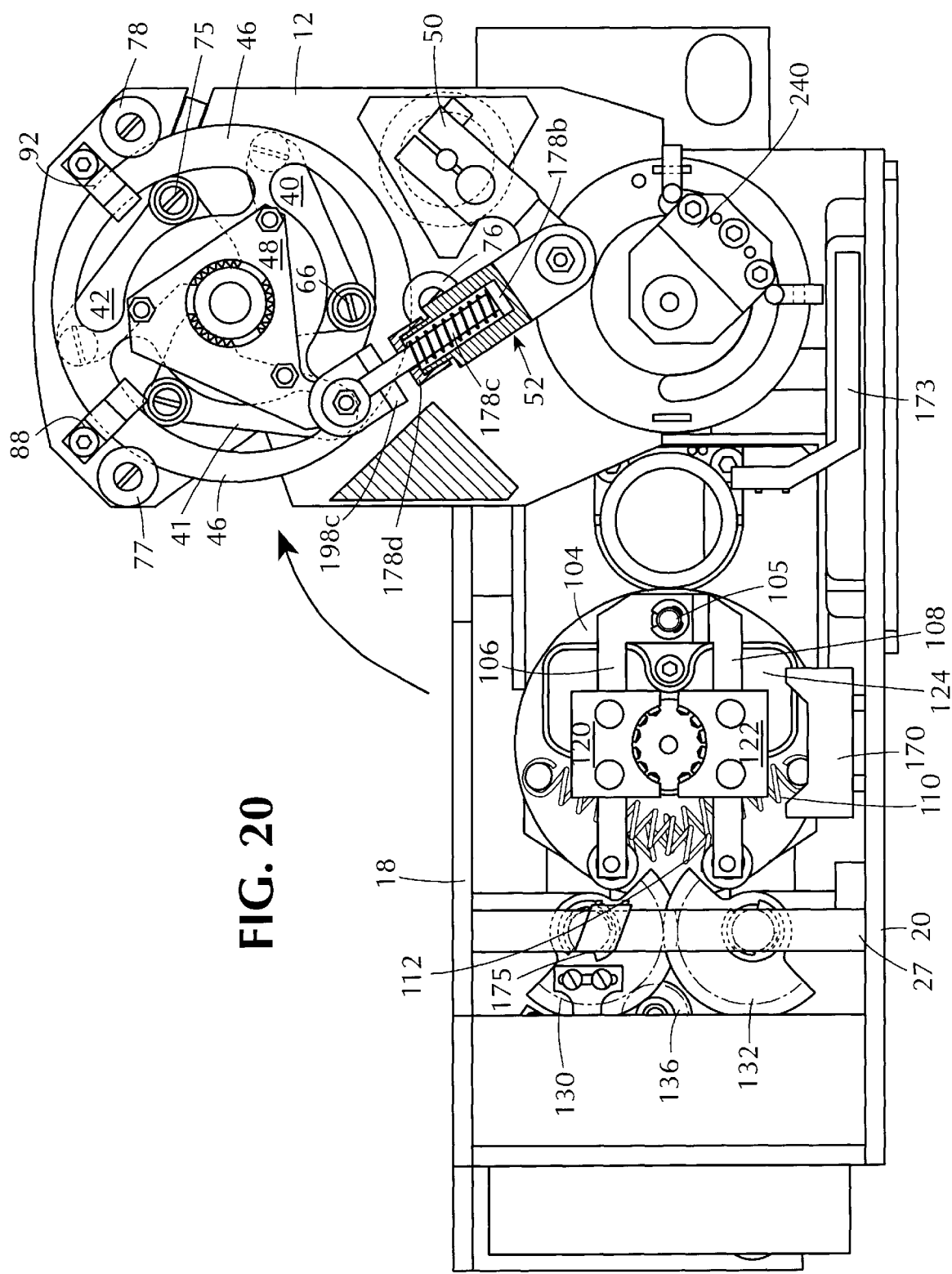
FIG. 20 is a top view of the decapper with the decapping arm returned to the first position now gripping a cap removed from a test tube (with the ultrasonic liquid level sensor and sensor holder removed, and the linkage for opening and closing the upper grippers shown in cutaway)
Figure 21:
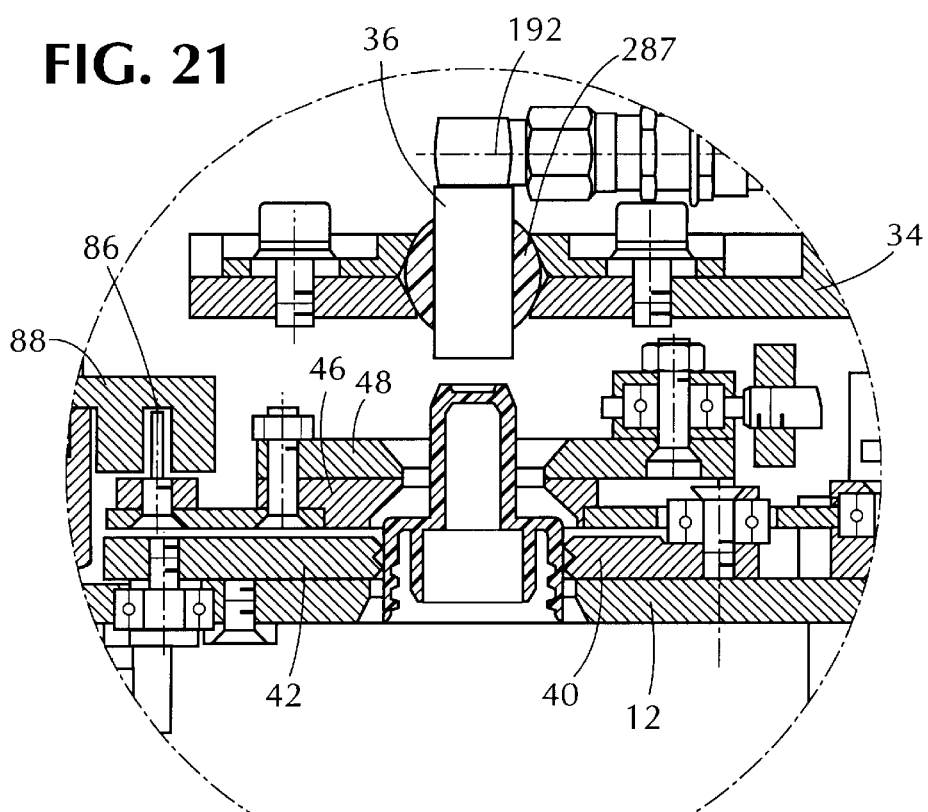
FIG. 21 is a rear, cutaway view of the upper grippers gripping the cap of FIG. 20.
Figure 22:
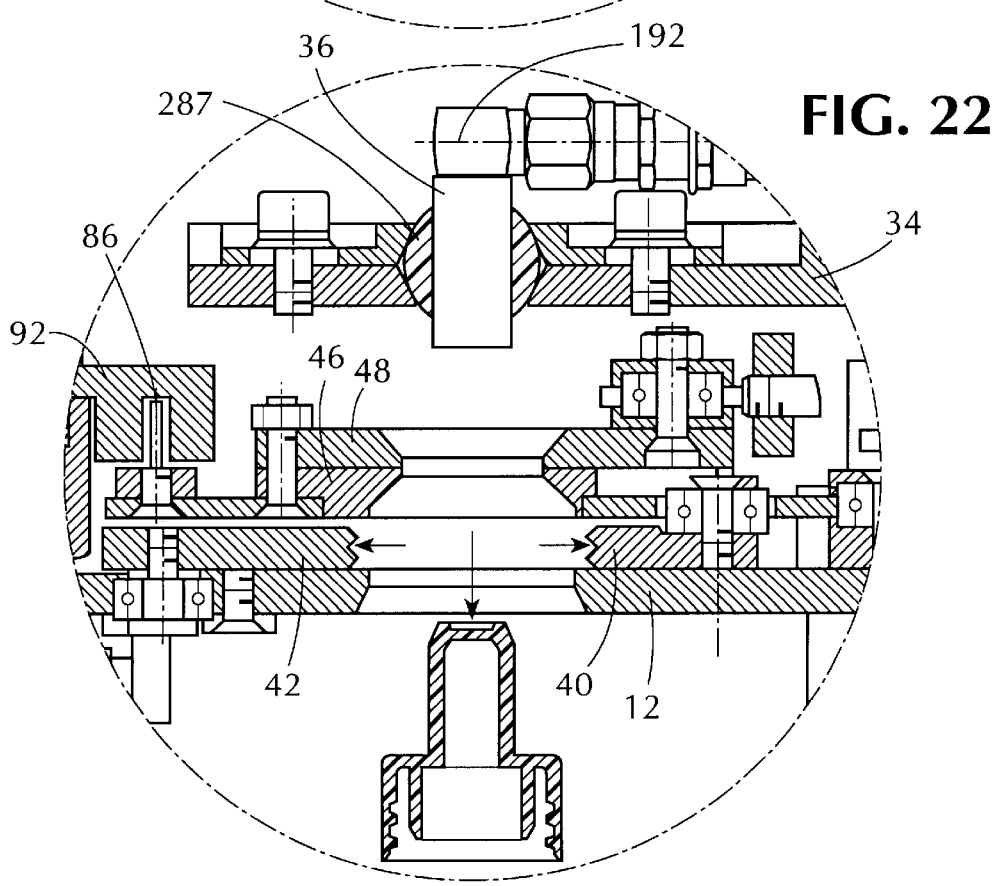
FIG. 22 is a rear, cutaway view of the upper grippers releasing the cap of FIG. 20.
Figure 23:
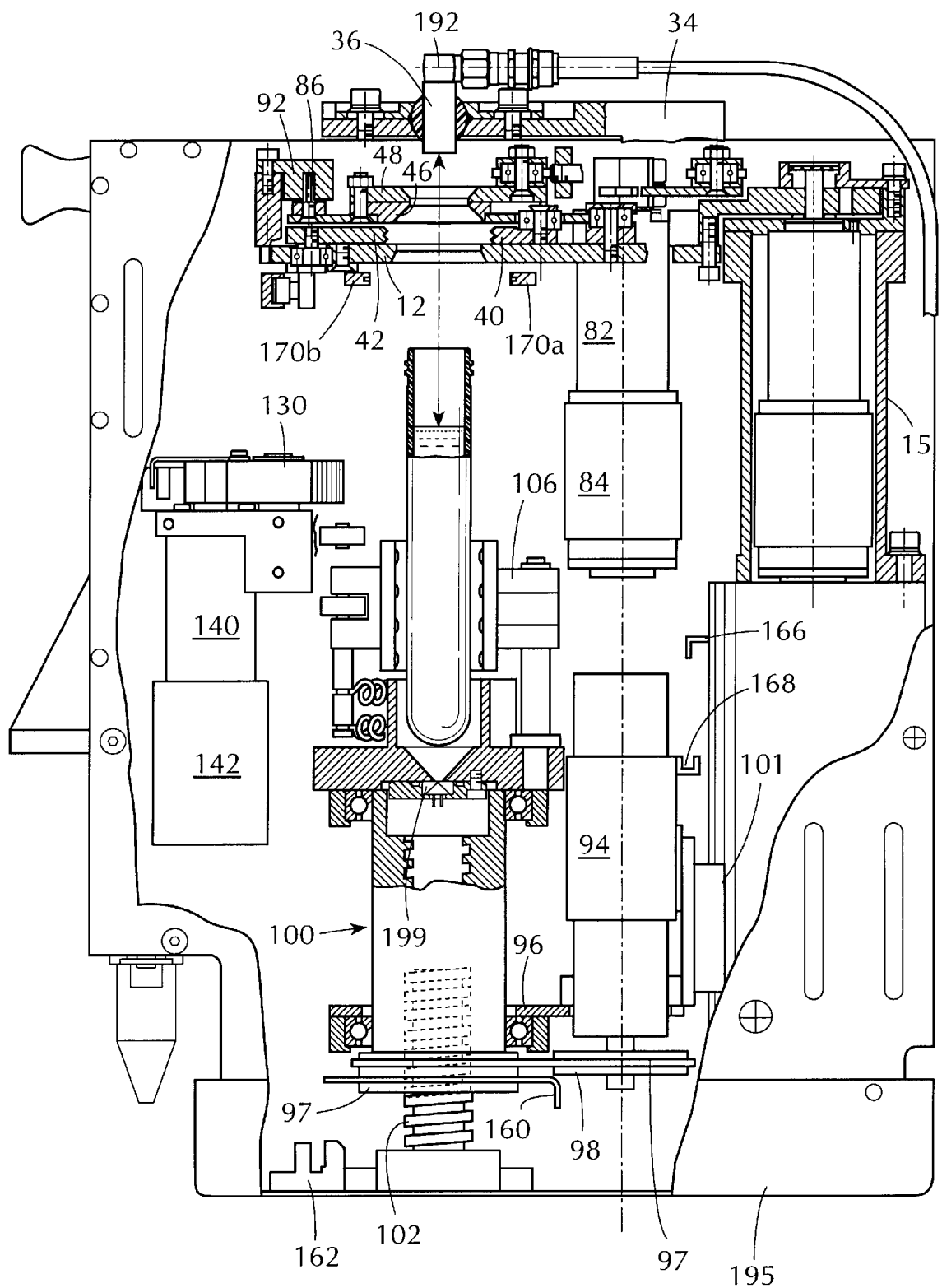
FIG. 23 is a rear, cutaway view of the decapper with the decapping arm returned to the second position a second time to read the liquid level in the test tube.

With the cap tightly gripped, rotatable assembly 100 rotates downward in a clockwise direction, thereby both pulling downward on the cap while twisting the cap. This downward motion of rotatable assembly 100 unscrews and removes screw-on caps, such as the Sarstedt cap shown in FIG. 17 or a commonly-used HemaGuard® cap which also must be unscrewed to be removed. This twisting and pulling motion also removes caps which must be pulled off, such as rubber stopper 190 which is removed as shown in FIGS. 18, 19 by gripping cap 190 in a fixed position between jaws 40–42 and rotating rotatable assembly 100 downward. This motion also decaps test tubes having any other type of cap which may be removed with a twisting motion. If the cap is not properly removed, this will be detected by sensor 170, which will prevent decapping arm 12 returning to the closed position to determine the liquid level in the test tube and hitting the cap.

The downward pulling motion of the test tube as the cap is being removed does not deform decapping arm 12 because of roller follower 29 which holds decapping arm 12 vertically in catch 27, as explained above. This downward pulling motion to remove the cap does, however, cause a small amount of vapor droplets to spray out of the test tube within decapper. To catch these droplets for easier cleaning of decapper 10, a disposable protective cover 270, having a central aperture 275 for the test tube, is mounted to the top of rotatable assembly (FIG. 27.). Protective cover 270 may be made of plastic and may be disposed of and replaced as part of a regular cleaning program for decapper 10.

After removing the cap, rotatable assembly 100 is rotated fully downward on lead screw 102 as indicated by the encoder on motor 94. The position of rotatable assembly 100 is confirmed by a flag 160 that triggers sensor 162. This provides a reference position in which the liquid level may be read. Decapping arm 12 then rotates to its open position while continuing to grip the removed cap. (FIGS. 20, 21) When sensor 32 detects that the decapping arm is in the decapping position, motor 84 is activated to rotate wheel 46 clockwise, which retracts jaws 40–42 and releases the removed cap. (FIG. 22) A waste container (not shown) may be positioned underneath upper grippers 22 when the decapping arm 12 is in the open position to catch the removed caps for disposal. Alternatively, the caps may be collected and used to recap the tubes with appropriate caps at a later time.

Figure 32:
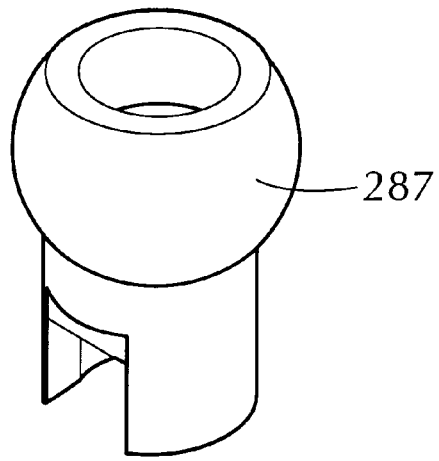
FIG. 32 is an isometric view of a gimbal in which an ultrasonic sensor is mounted.
Figure 33:
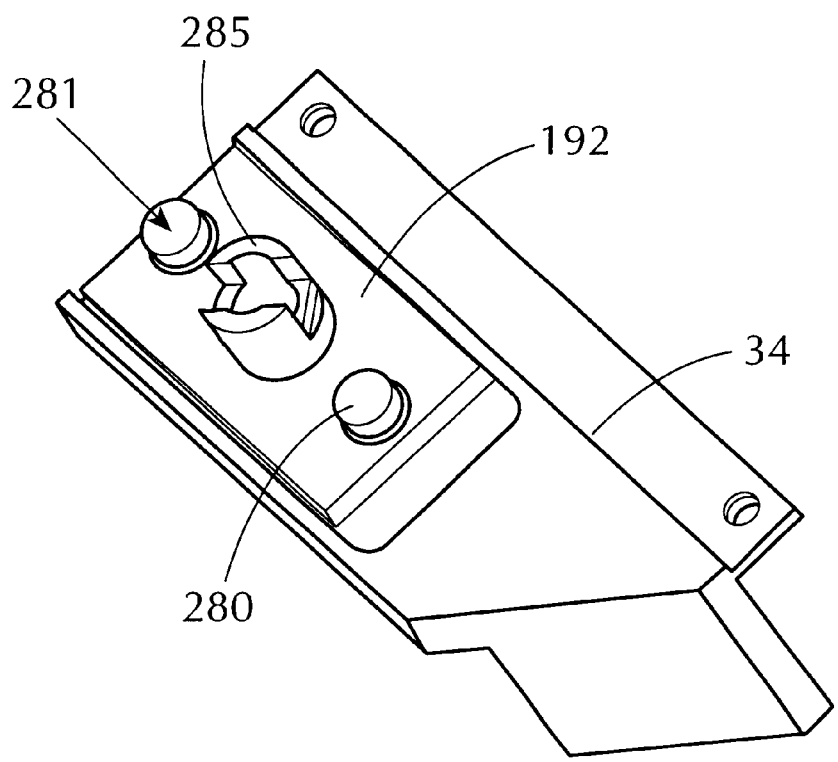
FIG. 33 is an isometric view of an armature in which the gimbal of FIG. 32 sits.

Decapping arm 12 next returns to the closed position with ultrasonic liquid level sensor 36 now positioned directly above the test tube still held by lower grippers 24. Sensor 36 sits in a sensor holder 192, which is a non-metallic swivel-type bracket which permits sensor 36 to be adjusted toward the surface of the liquid in the test tube. Sensor 36 is gimbaled within a gimbal 287 (FIG. 32) that sits within sensor holder 192 to self-align (FIG. 33) sensor 36 if instrument becomes misaligned and sensor 36 is held by sensor holder 192 above the transducer so as not to interfere with the ringing of the transducer with or limit the beam shape of the ultrasonic burst. Sensor holder 192 is adjusted to be properly aligned and is tightened with two set screws 280, 281 to armature 34 (FIG. 27). Sensor holder 192 is aligned to point sensor 36 perpendicularly to the liquid in the test tube.

Ultrasonic liquid level sensor 36 must be able to detect the liquid level within a short range from sensor 36. Because sensor 36 is unable to receive and detect echoes while sensor 36 is ringing, a dead zone is created adjacent sensor 36 through which the ultrasonic burst propagates before sensor 36 is able to detect echoes. Echoes reflected from a surface in the dead zone will not be detected at sensor 36. To avoid dead zone problems, sensor 36 is mounted at least approximately 1 inch from the top of the tallest test tube, which is 100 mm in height.

In a preferred embodiment, sensor 36 is preferably a Cosense sensor Part No. 123-10001. Sensor 36 has a transducer which is 0.25 inches in diameter and approximately 0.75 inches in length. A pulse having a frequency of approximately 1.0 MHz and a pulse width of approximately 1 microsecond is applied to sensor 36, causing sensor 36 to ring possibly as long as, but not longer than, 100 microseconds. When operated within these parameters, sensor 36 has a dead zone of approximately 12.7 mm (=0.5 inches). The high ultrasonic frequency of 1.0 MHz is used (typically ultrasonic sensors are operated in the kHz range) to reduce the length of ringing of the transducer, thereby minimizing the size of the dead zone. For the same reason, sensor holder 192 is nonmetallic so as not to extend the length of time the transducer rings. Leaving 1 inch between the dead zone and the tallest test tube and with sensor 36 having the given dimensions and operated at the specified frequency yields a sensing range of approximately 5 inches. To accommodate the required sensing range, sensor 90 should be mounted approximately 5 inches above the lowest point on which the test tube will rest, viz., on top of plate 111. The liquid level of the sample within the test tube is captured and transmitted to the sample handler controller or another external controller which requires the liquid level information.

Sensor 36 may be identical to and operated with the same operating conditions as the ultrasonic sensor used in the referenced application entitled Dynamic Noninvasive Detection of Analytical Container Features Using Ultrasound. The profiling described in that application may be used to determine at an earlier stage in the sample handler whether or not a test tube is capped. If the test tube is capped, it is sent to decapper 12 to be decapped.

After the liquid level is read, the test tube is removed from the decapper. (FIG. 25) To remove the test tube, decapping arm 12 is moved to the open position, the robotic arm returns to grip the now-uncapped test tube, and after a handshake between the robotic arm and decapper, lever arms 106, 108 are pushed apart by half-gears 130, 132 as described above. The robotic arm may then transport the test tube elsewhere.

If there is liquid in reservoir 124, the liquid may be detected by a sensor 199 mounted under void 107. (FIG. 24) Sensor 199 comprises an upper area 201, into which liquid from void 107 passes, prism 200, which may be comprised of optical glass, and two fiber optic cables 202, 204 pointing perpendicularly upward. Light is transmitted through fiber optic cable 202, as shown by arrow 206, and is incident on the side 207 of prism 200. If there is no liquid in the bottom of reservoir 124, the light incident on side 207 continues its upward travel and is not reflected. However, if there is liquid in reservoir 124, the change in the index of refraction from the optical glass of prism 200 to the liquid causes the bending of at least a portion of the light beam 206 in the direction of arrow 208 toward a second side of prism 209 and then downward in the direction of arrow 209 toward cable 204 where it is detected. This sensor provides the advantage that it is not subject to damage by liquid. In addition to reservoir 124, there is a tray 195 (FIG. 2) at the bottom of decapper frame 11 to catch spills not caught within reservoir 124. Tray 195 is removable for easy disposal of any liquid therein.

It should be understood from the design and above description of the present invention that decapper 10 is capable of decapping a variety of caps from test tubes of different types and various heights and diameters.

Besides decapping test tubes and measuring the liquid level of samples in the test tubes, where decapper 10 is a component in a sample handler, it may be used to reseat uncapped test tubes which are fed into the sample handler on racks but are not properly seated within the rack. As a result, the liquid level cannot be correctly measured by a liquid level sensor elsewhere in the sample handler because the liquid level measurement is made using a reference point set by the rack. If the sample handler is able to determine that the test tube is not properly seated using ultrasonic profiling, as described in the referenced Sample Handler application, and the data suggests that the test tube is an uncapped test tube but the liquid level in the test tube is too high, the test tube may be extracted from elsewhere in the sample handler by the robotic arm and transported to the decapper where the robotic arm seats the container properly within lower grippers 24. The sample handler controller instructs the decapper not to decap the test tube but does read the liquid level of the now properly seated test tube.

When used within an analytical instrument there will generally be constraints in which the decapper must complete the entire process of decapping a test tube and reading the liquid level. One of ordinary skill in the art will understand how to construct the decapper appropriately, including appropriate motor speeds, etc. to meet the particular design requirements.

One skilled in the art will recognize that the present invention is not limited to the above-described preferred embodiment, which is provided for the purposes of illustration and not limitation. Modifications and variations may be made to the above-described embodiment without departing from the spirit and scope of the invention.

We claim:

1. An automatic decapper for removing a cap from a test tube, said decapper comprising,
   a) a frame having upper and lower portions,
   b) an upper gripper device at the upper portion of the frame for gripping a cap of a capped test tube,
   c) a lower gripper device at the lower portion of the frame for gripping a body portion of the capped test tube below the cap,
   d) the upper gripper device including a plurality of movable upper gripper jaws having an open condition to permit disposition of the capped test tube in a decapping position wherein the cap of the capped test tube is located between the upper gripper jaws in their open condition, said cap having a peripheral portion and said upper gripper device including motor driven means joined to said upper gripper jaws for moving said upper gripper jaws into a selected upper gripping position to enable the upper gripper jaws to grip the peripheral portion of the cap of the capped test tube,
   e) said upper gripper jaws being non-rotatable about an axis through said capped test tube when the upper gripper jaws are in the selected upper gripping position, so as to render the gripped cap non-rotatable,
   f) the lower gripper device including a plurality of movable lower gripper jaws having an open condition to permit disposition of the body portion of the capped test tube between the lower gripper jaws in their open condition, said lower gripper device including motor driven means joined to said lower gripper jaws for moving the lower gripper jaws into a selected lower gripping position to enable the lower gripper jaws to grip the body portion of the capped test tube, and
   g) motor driven means joined to said frame for rotating and translating the lower gripper jaws about and along the axis through said capped test tube while the upper gripper jaws are in the non-rotatable upper gripping position on the cap of the capped test tube, to rotate the body portion of the capped test tube relative to the gripped cap and to lower the body portion of the capped test tube relative to the upper gripper jaw to thereby separate the body portion of the capped test tube from the gripped cap and thereby decap the capped test tube.

2. The decapper of claim 1 wherein said rotating and translating means comprise a rotatable assembly and a lead screw, said lower gripper jaws being mounted on the rotatable assembly, the rotatable assembly being coupled to the lead screw over which said rotatable assembly may be rotated and translated.

3. The decapper of claim 1 wherein each of said upper gripper jaws are pivotable from said open condition to the selected upper gripping position to grip said cap.

4. The decappper of claim 3 further comprising a decapping arm to which said upper gripper jaws are mounted, wherein said decapping arm is pivotable between a first position above said lower gripper jaws in which said capped test tube may be decapped and a second position which provides clearance adjacent said lower gripper jaws to allow the body portion of said test tube to be inserted into or removed from said lower gripper jaws or to release a removed cap for disposal.

5. An automatic decapper for removing a cap from a test tube, said decapper comprising
   upper grippers for gripping said cap, said upper grippers comprising,
       a rotatable disk having a plurality of arcuate slots,
       a plurality of retractable jaws coupled to said slots in said disk such that said jaws pivot to a gripping position to grip said cap with said jaws during decapping of said test tube and said jaws pivot to a retracted position when it is not desired to grip said cap, and
       means for rotating said disk to move said jaws between said retracted position and said gripping position,
   lower grippers for gripping said test tube,
   means for moving said lower grippers relative to said upper grippers to remove said cap from said test tube, and
   said decapper further comprising a decapping arm to which said upper grippers are mounted, wherein said decapping arm is pivotable between a first position above said lower grippers in which said test tube may be decapped and a second position which provides clearance adjacent said lower grippers to allow said test tube to be inserted into or removed from said lower grippers or to release a removed cap for disposal.

6. The decapper of claim 5 wherein said means for moving said lower grippers relative to said upper grippers to remove said cap from said test tube comprises means for rotating and translating said lower grippers downward while said upper grippers hold said cap stationary.

7. The decapper of claim 6 further comprising
   an assembly having a first side, a second side and a pivot point, the assembly pivot point being coupled to said decapping arm, the decapping arm pivoting to move between said first and second positions, said pivot point being located toward the first side of said decapping arm,
   a channel located above said lower grippers and adjacent the second side of said decapping arm opposite to said first side when said decapping arm is in said first position, and
   a cam on said second side of said decapping arm, said cam engagable with said channel when said decapping arm is in said first position to provide support for said decapping arm on said second side when said lower grippers are moved relative to said upper grippers.

8. The decapper of claim 7 wherein said channel comprises a ramp and said cam comprises a roller follower on said second side of said decapping arm that engages with said ramp.

9. The decapper of claim 5 wherein said decapping arm has a first aperture and said cap has an outer circumference and a raised central portion within said outer circumference, and said rotatable disk further comprises a second aperture located above said first aperture, said first and second apertures permitting said central portion to pass through and rise above said second aperture.

10. The decapper of claim 9 wherein said first and second apertures are axially aligned above a center of said test tube when said decapping arm is in said first position.

11. The decapper of claim 10 further comprising an armature for positioning an ultrasonic sensor above said first and second apertures and said test tube when said decapping arm is returned to said first position after said test tube has been decapped to determine a height level of a sample in said test tube.

12. An automatic decapper for removing a cap from a test tube, said decapper comprising
   upper grippers for gripping said cap, said upper grippers comprising,
       a rotatable disk having a plurality of arcuate slots, a plurality of retractable jaws coupled to said slots in said disk such that said jaws pivot to a gripping position to grip said cap with said jaws during decapping of said test tube and said jaws pivot to a retracted position when it is not desired to grip said cap, and means for rotating said disk to move said jaws between said retracted position and said gripping position, lower gripper for gripping said test tube, means for moving said lower grippers relative to said upper grippers to remove said cap from said test tube, and wherein said lower grippers comprise a pair of lever arms biased together toward a closed position to grip said test tube when said test tube is inserted therebetween, and said decapper further comprises a pair of half-gears that are rotatable to push apart said pair of lever arms from said closed position to an open position to accept or release a test tube when said pair of lever arms are adjacent said half-gears.

13. The decapper of claim 12 wherein said lower grippers further comprises a pinion coupled to at least one of said half-gears such that a rotation of said pinion causes a rotation of said half-gears.

14. The decapper of claim 12 wherein said lower grippers further comprises a pair of springs to bias said pair of lever arms toward said closed position.

15. An automatic decapper for removing a cap from a test tube, said decapper comprising upper grippers for gripping said cap, lower grippers for gripping said test tube, said lower grippers comprising a pair of lever arms biased together toward a closed position to grip said test tube when said test tube is inserted therebetween, a pair of half-gears that are rotatable to push apart said pair of lever arms from said closed position to an open position to accept or release a test tube when said pair of lever arms are adjacent said half-gears, and means for moving said lower grippers relative to said upper grippers to remove said cap from said test tube.

16. The decapper of claim 15 wherein said lower grippers further comprises a pinion coupled to at least one of said half-gears such that a rotation of said pinion causes a rotation of said half-gears.

17. The decapper of claim 16 wherein said lower grippers further comprises a pair of springs to bias said pair of lever arms toward said closed position.

18. The decapper of claim 15 wherein said upper grippers hold said cap stationary therein and said means for moving said lower grippers comprises a rotatable assembly to which said lower grippers is mounted and which is coupled to a lead screw over which said rotatable assembly may be rotated and translated downward.

19. A method for removing a cap from a capped test tube with a decapper comprising:

providing an automatic decapper for removing a cap from a test tube, said decapper comprising, a) a frame having upper and lower portions, b) an upper gripper device at the upper portion of the frame for gripping a cap of a capped test tube, c) a lower gripper device at the lower portion of the frame for gripping a body portion of the capped test tube below the cap, d) the upper gripper device including a plurality of movable upper gripper jaws having an open condition to permit disposition of the capped test tube in a decapping position wherein the cap of the capped test tube is located between the upper gripper jaws in their open condition, said cap having a peripheral portion and said upper gripper device including motor driven means joined to said upper gripper jaws for moving said upper gripper jaws into a selected upper gripping position to enable the upper gripper jaws to grip the peripheral portion of the cap of the capped test tube, e) said upper gripper jaws being non-rotatable about an axis through said capped test tube when the upper gripper jaws are in the selected upper gripping position, so as to render the gripped cap non-rotatable, f) the lower gripper device including a plurality of movable lower gripper jaws having an open condition to permit disposition of the body portion of the capped test tube between the lower gripper jaws in their open condition, said lower gripper device including motor driven means joined to said lower gripper jaws for moving the lower gripper jaws into a selected lower gripping position to enable the lower gripper jaws to grip the bode portion of the capped test tube, and g) motor driven means joined to said frame for rotating and translating the lower gripper jaws about and along the axis through said capped test tube while the upper gripper jaws are in the non-rotatable upper gripping position on the cap of the capped test tube, to rotate the body portion of the capped test tube relative to the gripped cap and to lower the body portion of the capped test tube relative to the upper gripper jaw to thereby separate the body portion of the capped test tube from the gripped cap and thereby decap the capped test tube h) gripping said test tube with said lower gripper jaws, i) inserting said cap within said upper gripper jaws while said upper gripper jaws are in said open condition;

j) gripping said cap by moving said upper gripper jaws to said upper gripping position, and k) removing said cap from said test tube by rotating and translating said lower gripper jaws away from said upper gripper jaws.

20. The method of claim 19 wherein said decapper further comprises a pivotable decapping arm to which said upper gripper jaws are mounted, said decapping arm having a first position in which said upper gripper jaws are located adjacent said lower gripper jaws and a second position in which said upper gripper jaws provide clearance adjacent said lower gripper jaws to allow the insertion or removal of said test tube from said lower gripper jaws said method further comprising:

before gripping said test tub, pivoting said decapping arm from said first position to said second position and inserting said test tube within said lower gripper jaws, and after gripping said test tube, rotating and translating said lower gripper jaws away from said first position of said decapping arm and pivoting said decapping arm back to said first position, wherein said step of inserting said cap into said upper gripper jaws comprises rotating and translating said lower gripper jaws to insert said cap of said capped test tube into said upper gripper jaws.

21. The method of claim 20 further comprising releasing said removed cap by moving said upper gripper jaws to said open condition and pivoting said decapping arm to said second position after said cap is removed from said test tube.

22. The method of claim 21 wherein said decapper further comprises an ultrasonic sensor located adjacent said uncapped test tube to measure a level of a sample in said test tube, and said method further comprises measuring said level of said sample using said ultrasonic sensor after said cap has been removed from said test tube.

23. The method of claim 19 wherein said lower gripper jaws comprise a pair of lever arms biased together toward said lower gripping position to grip said test tube when said test tube is inserted therebetween, and said decapper further comprises a pair of half-gears, and said method further comprises rotating and translating said lower gripper jaws until said lever arms are adjacent said half-gears, rotating said pair of half-gears in a first direction to push apart said pair of lever arms from said lower gripping position to said open condition to insert or release a test tube, and rotating said pair of half-gears in a second direction opposite said first direction to return said pair of lever arms to said lower gripping position.

24. The method of claim 19 further comprising inserting said test tube within said lower gripper jaws with a robotic arm.

* * * * *